US012599319B2

(12) United States Patent
Ben-Yoav et al.

(10) Patent No.: US 12,599,319 B2
(45) Date of Patent: Apr. 14, 2026

(54) ELECTROCHEMICAL DETECTION DEVICE AND METHOD

(71) Applicant: B.G. NEGEV TECHNOLOGIES AND APPLICATIONS LTD., AT BEN-GURION UNIVERSITY, Beer-Sheva (IL)

(72) Inventors: Hadar Shmuel Ben-Yoav, Ramat Gan (IL); Alon Mazafi, Ashkelon (IL)

(73) Assignee: B.G. NEGEV TECHNOLOGIES AND APPLICATIONS LTD., AT BEN-GURION UNIVERSITY, Beer-Sheva (IL)

( * ) Notice: Subject to any disclaimer, the term of this patent is extended or adjusted under 35 U.S.C. 154(b) by 0 days.

(21) Appl. No.: 16/618,944

(22) PCT Filed: Jun. 4, 2018

(86) PCT No.: PCT/IL2018/050603
§ 371 (c)(1),
(2) Date: Dec. 3, 2019

(87) PCT Pub. No.: WO2018/225058
PCT Pub. Date: Dec. 13, 2018

(65) Prior Publication Data
US 2020/0138344 A1 May 7, 2020

Related U.S. Application Data

(60) Provisional application No. 62/514,855, filed on Jun. 4, 2017.

(51) Int. Cl.
*A61B 5/145* (2006.01)
*A61B 5/1477* (2006.01)
(Continued)

(52) U.S. Cl.
CPC ...... *A61B 5/14507* (2013.01); *A61B 5/14546* (2013.01); *A61B 5/1477* (2013.01);
(Continued)

(58) Field of Classification Search
CPC ............ A61B 5/14507; A61B 5/14546; A61B 5/1477; A61B 2562/046; A61B 5/7267;
(Continued)

(56) References Cited

U.S. PATENT DOCUMENTS

2003/0011933 A1   1/2003   Tsuchiyama et al.
2003/0146110 A1   8/2003   Karinka et al.
(Continued)

FOREIGN PATENT DOCUMENTS

WO        2007/096849         8/2007

OTHER PUBLICATIONS

Kim, E., Chocron, S.E., Ben-Yoav, H., Winkler, T.E., Liu, Y., Glassman, M., Wolfram, C., Kelly, D.L., Ghodssi, R. and Payne, G.F. (2015), Programmable "Semismart" Sensor: Relevance to Monitoring Antipsychotics. Adv. Funct. Mater., 25: 2156-2165. https://doi.org/10.1002/adfm.201403783 (Year: 2015).*
(Continued)

*Primary Examiner* — Jason M Sims
*Assistant Examiner* — Kyle W. Kretzer
(74) *Attorney, Agent, or Firm* — Nixon & Vanderhye PC

(57) ABSTRACT

An electrochemical sensor comprising a counter electrode, optionally a reference electrode, and an array of multiple working electrodes, wherein at least one of the working electrodes is a film-coated electrode, and wherein the film-forming material has repeat unit that comprises six-membered non-aromatic ring. A device for electrochemical detec-
(Continued)

tion that comprises the sensor (an electrochemical tongue) and a method for detecting analytes with the aid of the sensor are also disclosed.

29 Claims, 13 Drawing Sheets

(51) Int. Cl.

| | |
|---|---|
| *G01N 27/327* | (2006.01) |
| *G01N 33/493* | (2006.01) |
| *G06N 3/02* | (2006.01) |
| *G16H 50/20* | (2018.01) |

(52) U.S. Cl.
CPC ....... *G01N 27/3277* (2013.01); *G01N 33/493* (2013.01); *G06N 3/02* (2013.01); *G16H 50/20* (2018.01); *A61B 2562/046* (2013.01)

(58) Field of Classification Search
CPC ............. A61B 5/0022; G01N 27/3277; G01N 33/493; G06N 3/02; G16H 50/20
See application file for complete search history.

(56) References Cited

U.S. PATENT DOCUMENTS

| | | | |
|---|---|---|---|
| 2005/0211571 A1* | 9/2005 | Schulein ............ | G01N 27/3277 205/792 |
| 2007/0172821 A1 | 7/2007 | Wu et al. | |
| 2013/0274574 A1 | 10/2013 | Say et al. | |
| 2014/0118138 A1* | 5/2014 | Cobelli ................ | A61B 5/4866 340/539.12 |
| 2014/0332410 A1* | 11/2014 | Ben-Yoav .......... | G01N 15/1056 204/403.01 |
| 2016/0025678 A1 | 1/2016 | Kurup et al. | |
| 2017/0101662 A1* | 4/2017 | Liu .................... | G01N 27/3277 |
| 2017/0370870 A1* | 12/2017 | Fomina .................... | C25D 3/48 |

OTHER PUBLICATIONS

Bouchikhi, B., Ionescu, R., El Hassani, N.E.A., El Bari, N., Tahri, K., Saidi, T., Discrimination and identification of various volatile organic compounds in human urine using a voltammetric electronic tongue and pattern recognition methods. Advances in Information Technology: Theory and Application, 2016. 1(1).

Cetó, X., Voelcker, N.H., Prieto-Simon, B., Bioelectronic tongues: New trends and applications in water and food analysis. Biosensors and Bioelectronics, 2016. 79: p. 608-626.

Cipri, A., Schulz, C., Ludwig, R., Gorton, L., del Valle, M., A novel bio-electronic tongue using different cellobiose dehydrogenases to resolve mixtures of various sugars and interfering analytes. Biosensors & Bioelectronics, 2016. 79: p. 515-521.

Kim, E., Chocron, S.E., Ben-Yoav, H., Winkler, T.E., Liu, Y., Glassman, M., Wolfram, C., Kelly, D.L., Ghodssi, R., Payne, G.F., Programmable "semismart" sensor: Relevance to monitoring antipsychotics. Adv Funct Mater, 2015. 25(14): p. 2156-2165.

Silue, T.et al: Chitosan-Catechol Modified Dopamine Sensor; Abstracts. The Electrochemical Society, 2017, p. 1109.

Wadehra, A., Patil, P.S., Application of electronic tongues in food processing. Analytical Methods, 2016. 8(3): p. 474-480.

Yi Cheng, Xiaolong Luo, Jordan Betz, Gregory F. Payne, William E. Bentley and Gary W. Rubloff, Mechanism of anodic electrodeposition of calcium alginate, Soft Matter, 7, 5677-5684, 2011.

International Search Report for PCT/IL2018/050603 dated Aug. 26, 2018, 6 pages.

Written Opinion of the ISA for PCT/IL2018/050603 dated Aug. 26, 2018, 5 pages.

Bouchikhi, B., Ionescu, R., El Hassani, N.E.A., El Bari, N., Tahri, K., Saidi, T., Discrimination and identification of various volatile organic compounds in human urine using a voltammetric electronic tongue and pattern recognition methods. Advances in Information Technology: Theory and Aoolication, 2016. 1(1).

Cet6, X., Voelcker, N.H., Prieto-Simon, B., Bioelectronic tongues: New trends and applications in water and food analysis. Biosensors and Bioelectronics, 2016. 79: p. 608-626.

* cited by examiner

| Samples | Current values [$\mu A$] |
|---|---|
| | 5 NE + 25 DA bare; 5 NE + 25 DA Modified |
| | 10 NE bare + 20 DA bare; 10 NE + 20 DA Modified |
| | ⋮ |

Fig. 11
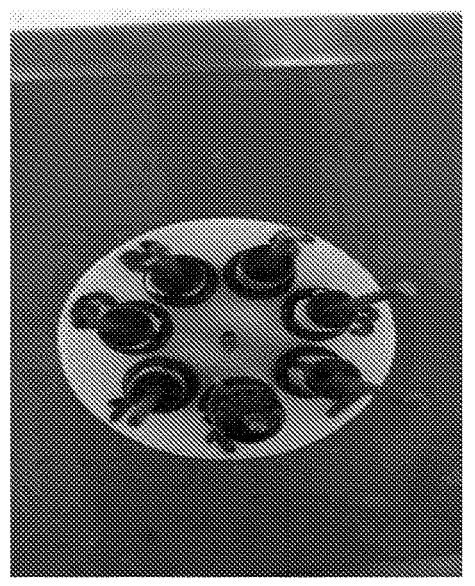 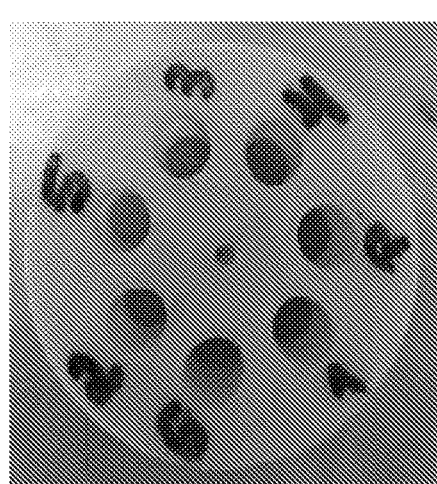
Fig. 12
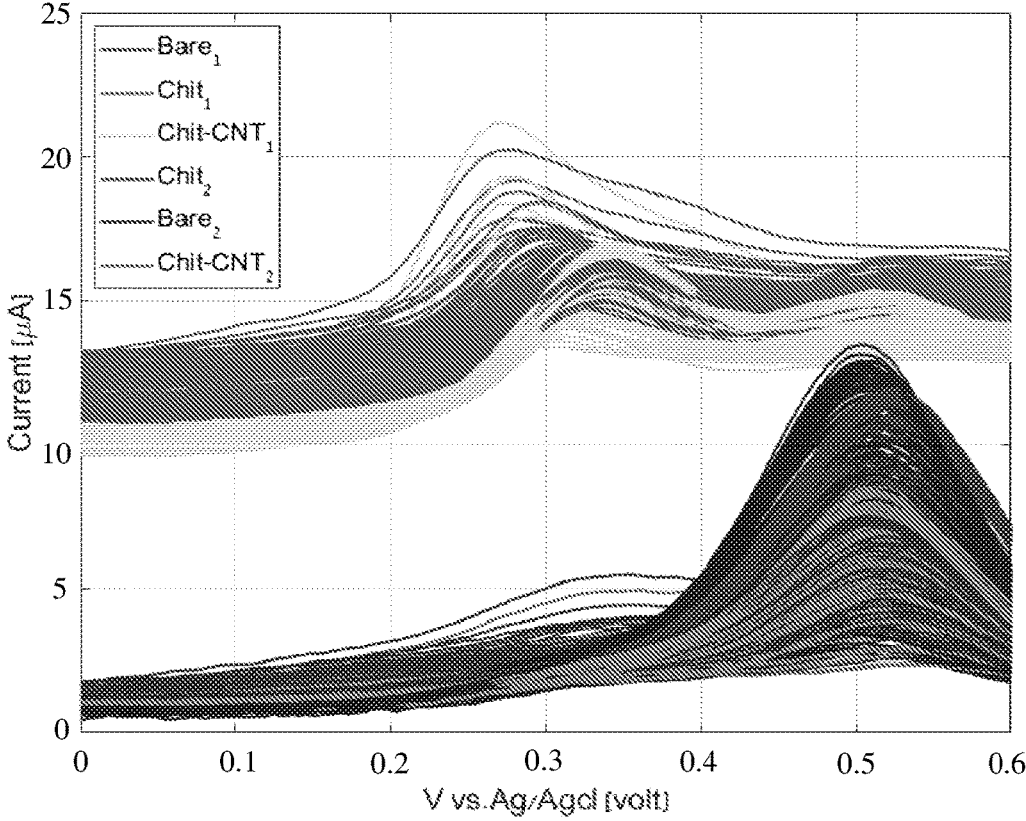

Fig. 15
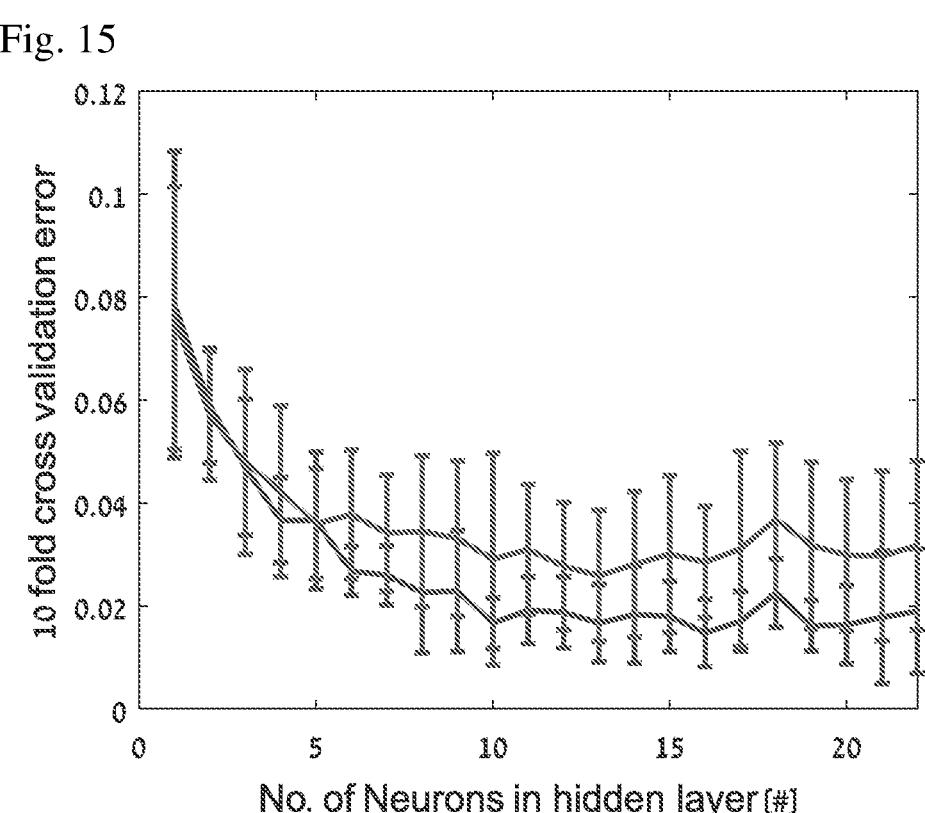
Fig. 16A                  Fig. 16B
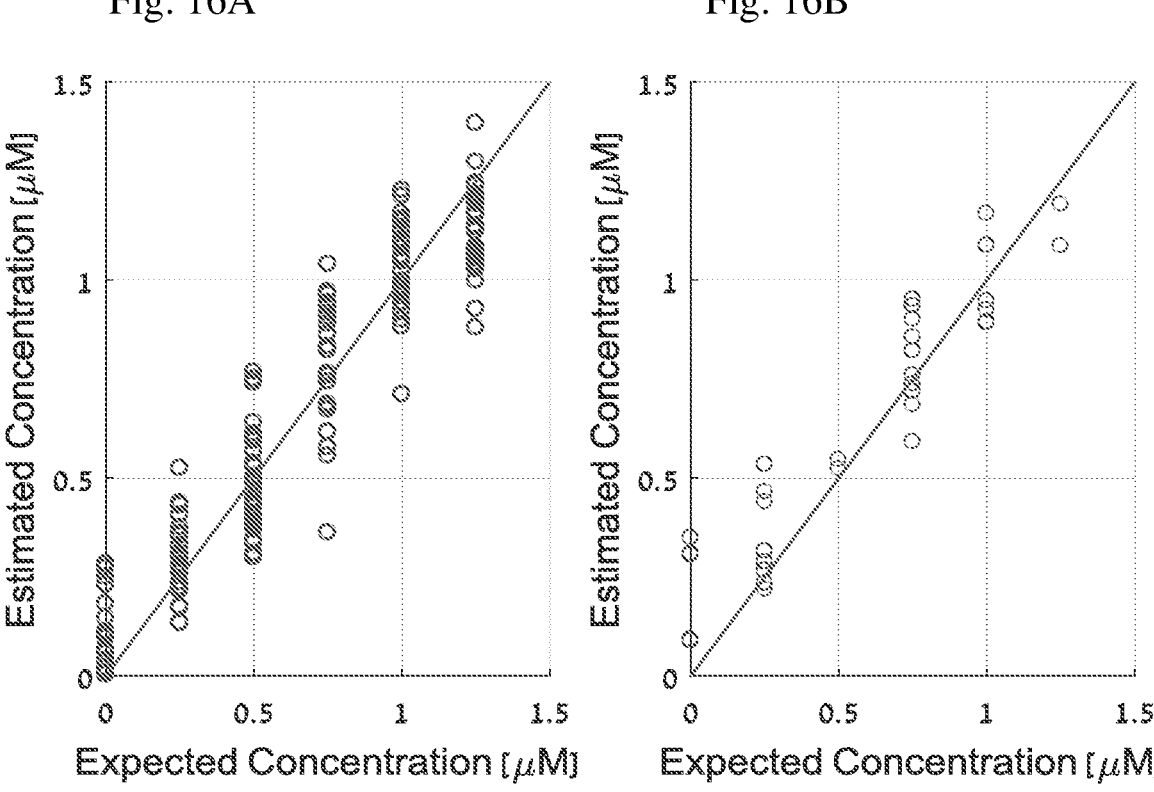

ELECTROCHEMICAL DETECTION DEVICE AND METHOD

CROSS-REFERENCE TO RELATED APPLICATIONS

This application is the U.S. national phase of International Application No. PCT/IL2018/050603 filed Jun. 4, 2018 which designated the U.S. and claims priority to U.S. Provisional Patent Application No. 62/514,855 filed Jun. 4, 2017, the entire contents of each of which are hereby incorporated by reference.

BACKGROUND AND SUMMARY

Continuous monitoring of multiple diagnostic biological and chemical markers in biofluids can provide important and dynamic 'biomolecular feedback' about the physiological conditions of patients, thus enabling early disease detection and promoting personalized therapy. However, most continuous monitoring approaches currently suffer from delayed responses and a long duration between diagnostic tests, which limit the ability of doctors and caregivers to rapidly adjust treatment or medication dosage. Thus, a more efficient scheme for such continuous monitoring requires the development of low-cost analytical micro-devices ("portable laboratories"), in which the sensor continuously measures the in situ levels of unlabeled redox-active diagnostic markers in the sample.

Electrochemical sensors, which generate a unique signal according to the redox state of a molecule of interest, are well suited for this analytical task. These translational and low-cost analytical technologies can continuously measure the in situ levels of multiple unlabeled molecules based on their redox state in the sample.

For example, one major electrochemical technique is voltammetry. An illustrative measurement set-up consists of a working electrode, a counter electrode and optionally a reference electrode electrically connected to a potentiostat. The current at the working electrode is measured as the potential applied across the working electrode and the counter electrode is varied linearly with time. When electroactive species are present in the tested sample, they undergo oxidation (or reduction) when the potential on the working electrode is sufficiently positive (or negative). The oxidation/reduction electrochemical reactions are manifested by an increase in the current (anodic or cathodic) measured; that is, creation of an electrochemical signal with magnitude and position characteristic of a given analyte.

However, for samples containing more than one type of redox molecule (such as biofluids), several redox molecules in the sample generate overlapping electrochemical signals that contribute to the background signal, decreasing the quality of the transduced redox information. The resulting complex electrochemical signal can undergo digital deconvolution through direct and simple signal processing methods. Naturally, however, the level of complexity increases as a function of the number of molecules in the solution, making such a separation impractical for solutions with multiple redox molecules—and practically impossible when these molecules have overlapping electrochemical signals.

The difficulty that arises in detecting and measuring the concentration of analytes of interest, when multiple electrochemically active molecules are present in the tested sample, is illustrated in connection with detection in a biofluid of two neurotransmitters, dopamine and norepinephrine, as shown in FIGS. 1A-1C. These two compounds are amenable to electrochemical detection, seeing that they are redox molecules that can undergo two-electron redox reactions, transforming into dopamine-o-quinone and norepinephrine quinone, respectively. However, as pictorially shown in FIGS. 1A-1C, overlapping electrochemical signals are generated by voltammetry. In addition, the presence of uric acid—another electroactive species—introduces a further complexity, because uric acid generates a strong electrochemical signal that masks the signals produced by the neurotransmitters, that is, uric acid acts as interferant.

Instead of using selective electrodes with high specificity to the analytes of interest, there is an alternative approach towards differentiating between interfering redox-active molecules generating overlapping electrochemical signals that is based on the use of electrochemical tongue, e.g., a sensor adapted for voltammetry measurements using an array of non-selective working electrodes which differ from one another. The complex pattern of electrochemical signals generated by multiple redox molecules present in the tested sample is then analyzed with advanced pattern recognition algorithms.

For example, US 2003/011933 and WO 2007/096849 describe an analysis system comprising a counter electrode, a reference electrode and a set of working electrodes that are made of different noble metals. The data recorded is analyzed using multivariate model, e.g., artificial neural models.

US 2016/0025678 deals with detection of metal ions using an electrochemical tongue comprising a plurality of working electrodes that are surface-modified; the electrodes are coated with polymer films to which a chelating agent is bonded.

Other examples of 'voltammetric electronic tongue' integrating electrochemical sensors with sophisticated pattern recognition algorithms to facilitate the in situ analysis of complex electrochemical signals generated by multiple redox molecules were described by Bouchikhi, B., Ionescu, R., El Hassani, N. E. A., El Bari, N., Tahri, K., Saidi, T., *Discrimination and identification of various volatile organic compounds in human urine using a voltammetric electronic tongue and pattern recognition methods*. Advances in Information Technology: Theory and Application, 2016. 1(1); Cipri, A., Schulz, C., Ludwig, R., Gorton, L., del Valle, M., A novel bio-electronic tongue using different cellobiose dehydrogenases to resolve mixtures of various sugars and interfering analytes. Biosensors & Bioelectronics, 2016. 79: p. 515-521; Wadehra, A., Patil, P. S., Application of electronic tongues in food processing. Analytical Methods, 2016. 8(3): p. 474-480 and Cetó, X., Voelcker, N. H., Prieto-Simon, B., Bioelectronic tongues: New trends and applications in water and food analysis. Biosensors and Bioelectronics, 2016. 79: p. 608-626.

The present invention provides an electrochemical sensor comprising an array of partially selective ('semi-selective') electrodes that can simultaneously cross-react with multiple redox molecules in the mixture. The cross-reactivity is achieved by combining together (i) bare electrodes, (ii) film-coated electrodes (in particular electrodeposited film-coated electrodes) and (iii) conductive additives-incorporated film-coated electrodes (e.g., using conductive additive that co-deposit with the film-forming material onto the electrodes). That is, the electrochemical sensor disclosed herein utilizes a set of electrodes that are surface-modified with materials that possess different electron and mass transfer rates, thereby generating slightly diverse electrochemical signals from the analyzed redox-active mixture. Hitherto, a film-coated electrode was tested individually to improve the selectivity towards detecting an analyte of interest in multicomponent mixtures (Kim, E., Chocron, S. E., Ben-Yoav, H., Winkler, T. E., Liu, Y., Glassman, M., Wolfram, C., Kelly, D. L., Ghodssi, R., Payne, G. F., Programmable "semismart" sensor: Relevance to monitoring antipsychotics. Adv Funct Mater, 2015. 25(14): p. 2156-2165.

The present invention is therefore primarily directed an electrochemical sensor comprising a counter electrode, optionally a reference electrode, and an array of multiple working electrodes, wherein at least one of the working electrodes is a film-coated electrode, and wherein the film-forming material has repeat unit that comprises six-membered non-aromatic ring. For example, the film-forming material is a polysaccharide, e.g., chitosan.

Also provided is a device (an electrochemical tongue) for electrochemical detection, comprising a counter electrode; optionally a reference electrode; an array of multiple working electrodes as described herein; a potentiostat or galvanostat to which the electrodes are electrically connected to allow control of the potential or current of the working electrodes, respectively, to create a data set of electrochemical signals when the electrodes are immersed in a sample; and a processor configured for analyzing a data set of electrochemical signals by one or more chemometric techniques.

The present invention also provides a method of electrochemical detection of one or more analytes in a liquid sample, the method comprising the steps of:

bringing a liquid sample into contact with the electrochemical sensor described herein;

applying variable voltage, fixed voltage, current or impedance across the working electrodes;

measuring the current flowing or the impedance between each of the working electrodes and a counter electrode, or the potential between each of the working electrodes and a reference electrode, to obtain a raw data set consisting of plurality of electrochemical signals;

preprocessing the raw data electrochemical signals; and applying chemometric method(s) to the preprocessed data, to qualitatively or quantitively characterize the analyte of interest.

BRIEF DESCRIPTION OF THE DRAWINGS

FIG. 11 shows an experimental setup;

FIG. 12 shows the electrochemical signals recorded for a set of samples.

FIG. 15 plots the validation error against the number of neurons in the hidden layer;

FIGS. 16A and 16B graphically illustrates the performance of the model, in the form of estimated (model-predicted) concentration versus expected (real) plot;

DETAILED DESCRIPTION

A preferred embodiment of the invention is directed to the analysis of biofluid samples (urine, blood, saliva), e.g., for determining the presence and concentration of neurotransmitters (dopamine and/or norepinephrine). Experimental results reported below indicate that this can be achieved with the aid of voltammetry (applying varied voltage and measuring current as the analyte signal), such as differential pulse voltammetry. However, other organic redox-active molecules may be quantified with the method of the invention using different electrochemical techniques.

Figure 1A:
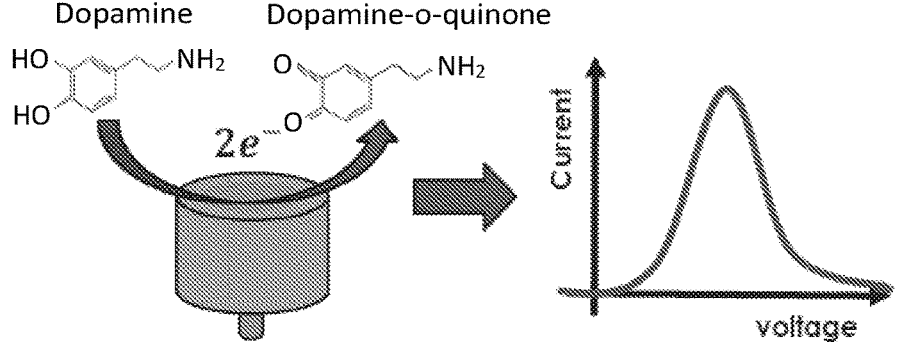
FIG. 1A illustrates the electrochemical signal of dopamine (DA)
Figure 1B:
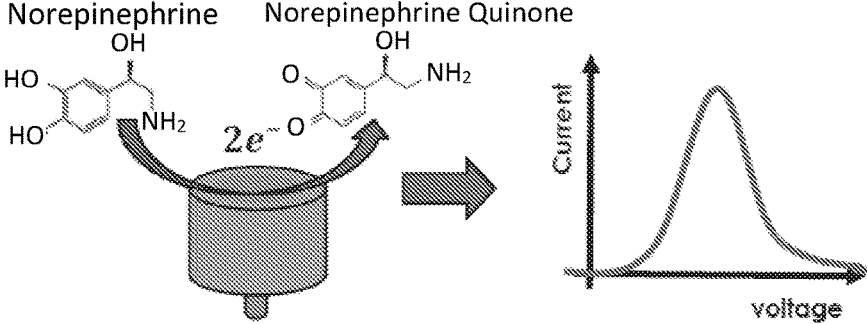
FIG. 1B illustrates the electrochemical signal of norepinephrine (NE)
Figure 1C:
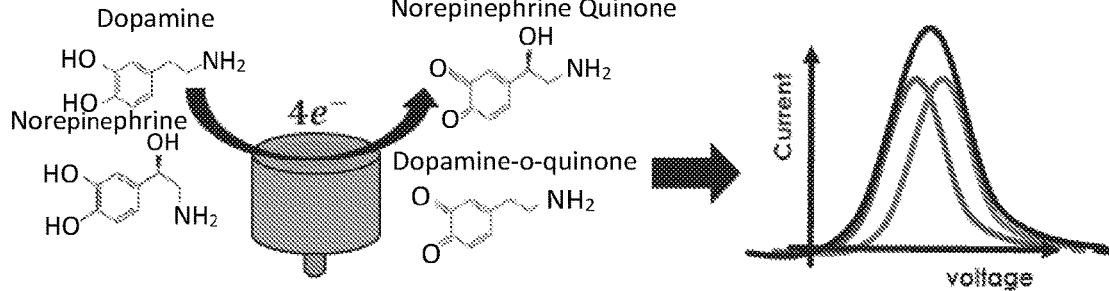
FIG. 1C illustrates the combined electrochemical signal of dopamine and norepinephrine.
Figures 2, 3:
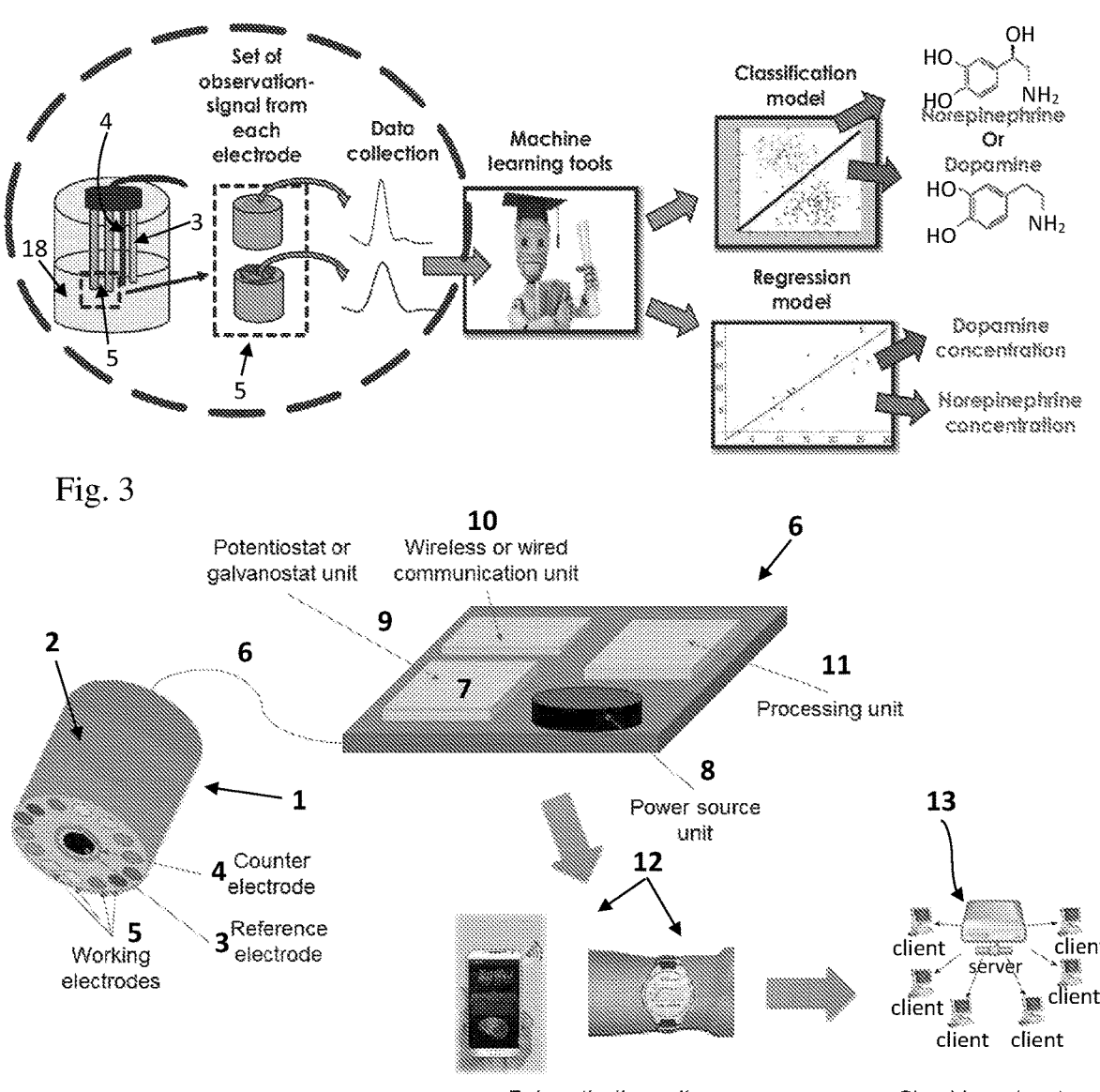
FIG. 2 illustrates how the present invention approaches the problem of electrochemically distinguishing between the neurotransmitters dopamine and norepinephrine when they are both present in a liquid sample.
FIG. 3 provides a schematic illustration of the electrochemical sensor according to the invention and a detection device into which the sensor is incorporated.

FIG. 2 illustrates how the present invention approaches the problem of electrochemically distinguishing between the neurotransmitters dopamine and norepinephrine when they are both present in a liquid sample, despite the fact that these molecules generate overlapping electrochemical signals. In FIG. 2, an array consisting of two working electrodes is shown for the purpose of simplicity. The working electrodes include a bare gold electrode and chitosan-coated gold electrode. The working electrodes (5) are marked in a dashed rectangle; the other two electrodes seen in FIG. 2 are the counter (4) and reference (3) electrodes. The electrodes are immersed in a liquid sample (18) that contains the two molecules. By combining the readings of all working electrodes—each produces a slightly different electrochemical signal, as seen in FIG. 2—and analyzing the combined reading with computational mathematical algorithms, the concentrations of the individual redox-active molecules dopamine and norepinephrine in a tested sample can be determined, as explained in more detail below. It should be noted that the invention is not limited to the analysis of dopamine and norepinephrine in a liquid sample; it allows differentiation between other organic redox-active molecules which are otherwise inseparable from one another owing to the overlapping electrochemical signals they generate.

Preferably, the array of working electrodes comprises a first subarray consisting of one or more bare electrode, a second subarray consisting of one or more film-coated working electrodes and/or a third subarray consisting of one or more conductive additive-incorporated film-coated electrodes.

Working electrodes of the same subarray may be the same (to enable duplicate measurements to be averaged) or different (to achieve enhanced sensitivity: two distinct bare electrodes which differ from one another in the electrode material; two distinct film-coated electrodes may differ from one another in the film material and/or film thickness; and conductive additive-incorporated film-coated electrodes may differ from one another in the loading level of the additive.

More specifically, the electrochemical sensor comprises an array consisting of a total of n working electrodes ($3 \leq n \leq 50$, preferably $3 \leq n \leq 30$, e.g., $3 \leq n \leq 10$) subdivided to include k bare electrodes ($1 \leq k \leq n/2$, for example, $1 \leq k \leq n/3$), m film-coated working electrodes ($1 \leq m \leq n-k$), preferably at least two film-coated electrodes) and p conductive additive-incorporated film-coated electrodes ($1 \leq p \leq n/3$). For example, experimental results reported below indicate that an array composed of three subarrays that are equal in size (k=m=p=2; that is, a total of six working electrodes) constitutes an efficient sensor for neurotransmitters monitoring in a biofluid; but for other applications smaller or larger arrays could be fabricated.

The working electrodes are preferably made of noble metals, e.g., gold, platinum, rhodium and iridium; gold is generally preferred, both for use as a bare electrode and as the base electrode of the film-coated electrodes. But other electrodes, such as glassy carbon electrodes, can also be incorporated into the array of working electrodes. For some purposes a single bare electrode in the array would suffice; but for particularly challenging analytical tasks two or more bare electrodes can be used. In such cases, bare electrodes of distinct materials are mounted in the array.

Turning now to the film-coated electrodes, a preferred film-forming material is a polymer having a six-membered, non-aromatic ring in the repeating unit, bearing chemical group that becomes charged in solution, such as amine, hydroxyl, carboxylic acid and sulfonic acid.

Different techniques may be used to create the film coating onto the electrode surface, but preferably, the working electrodes are electrodeposited film-coated electrodes. For example, polysaccharides such as chitosan (an amino-substituted polysaccharide) and alginate (an acidic polysaccharide) lend themselves to electrodeposition owing to their pH-dependent hydrogel-forming properties. Importantly, useful additives present in the deposition solution of these polymers will co-deposit to become part of the film, thereby modifying its properties and improving the sensitivity of the array. Preferred additives are conductive additives selected from the group consisting of carbon nanotubes (abbreviated herein CNT), gold nanoparticles and platinum nanoparticles.

In general, electrodeposition of the film onto the electrode surface could be accomplished from a deposition solution with the aid of (i) galvanostatic method, with constant current density set in the range from 1 to 10 A m$^{-2}$,(ii) potentiostatic method, at a constant potential set in the range between 0.8 and 1.5 V; or (iii) cyclic voltammetry.

For example, electrodeposited chitosan film-coated electrode can be prepared with the aid of a deposition solution with chitosan concentration in the range from 0.5 to 2 wt %, preferably from 0.8 to 1.2 wt %. The cleaned, polished electrode (e.g., gold electrode) to be coated is immersed in the solution and biased to the negative potential against a counter electrode with constant (cathodic) current being applied between the electrodes for a period of time of 0.5 to 5 min, supplied by a DC current source; typically the current is set in the range from 4 to 6 A/m$^2$.

For example, electrodeposited alginate film-coated electrode can be prepared with the aid of a deposition solution with alginate concentration in the range from 0.5 to 2 wt %, e.g., from 0.8 to 1 wt %, and CaCO$_3$ in the range from 0.1 to 1 wt %, preferably from 0.2 to 0.3 wt %. In this case the electrode to be coated is the anode, as described for example, in Yi Cheng, Xiaolong Luo, Jordan Betz, Gregory F. Payne, William E. Bentley and Gary W. Rubloff, Mechanism of anodic electrodeposition of calcium alginate, Soft Matter, 7, 5677-5684, 2011.

As pointed out above, conductive additives can be included in the deposition solution; these additives will co-deposit and affect the film properties. The concentration of the additives in the deposition solution is in the range from 0.1 to 2%, preferably from 0.8 to 1.25 wt %.

Upon completion of the electrodeposition, the film-coated electrodes, or additive-incorporated film-coated electrode, are rinsed to remove non-deposited material and are ready for use in the array of the invention.

Accordingly, another aspect of the invention is a process for preparing an electrochemical sensor described above, comprising preparing a deposition solution of the film-forming material (e.g., of the polysaccharide), electrodepositing said film-forming material onto an electrode surface to create film-coated electrode, wherein a conductive additive that is optionally present in said solution is co-deposited onto the electrode surface, and assembling the coated electrode with one or more bare working electrodes, a counter electrode and optionally a reference electrode to form the sensor.

The aforementioned techniques enable the formation of films of different thickness in the range of 0.05 to 5 μm and with different loading levels of the conductivity additives. For example, an array according to the invention may include two or more film-coated working electrodes; in one electrode, the thickness of the film coating is in the range from 0.2 to 0.3 μm and in the other electrode the thickness of the film coating is in the range from 0.3 to 0.4 μm.

In one preferred electrochemical sensor of the invention, the array of working electrodes comprises:
one or more gold bare electrodes; and
one or more chitosan-coated gold electrodes.
In another preferred electrochemical sensor of the invention,
the array of working electrodes comprises:
one or more gold bare electrodes;
one or more chitosan-coated gold electrodes; and
one or more carbon nanotubes-incorporated chitosan-coated gold electrodes.

Another type of film-forming material that could be electrodeposited to create film-coated electrode for use in the electrochemical sensor of the invention is reduced graphene oxide. The deposition solution is prepared by known methods, e.g., the Hummers' method, where oxidation of graphite flakes or powder takes place upon adding the graphite to a cold solution of sulfuric acid (e.g., 0° C.) followed by gradual addition of sodium nitrate and potassium permanganate under continuous stirring. For example, on a laboratory scale, the addition time of each of the successively added NaNO$_3$ and KMNO$_4$ reagents is not less than ten to fifteen minutes. On completion of reagent's addition, the reaction mixture is heated to about 35-45° C. and kept under stirring for a couple of hours, e.g., not less than two hours. The reaction is terminated by addition of water and hydrogen peroxide which removes excess permanganate. The graphene oxide is recovered by centrifugation and freeze dried and used to prepare deposition solution with concentrations in the range from 0.1 to 0.9 mg/ml GO. Additional procedures are described below. Next, r-GO is obtained electrochemically from the GO solution onto the electrode (Au), using cyclic voltammetry as illustrated below.

The array of multiple working electrodes comprises a set of film-coated working electrodes which differ from one another in one or more of the following features: film material, film thickness, film density and loading level of conductivity additives that are incorporated into the film, such that the working electrodes used in the electrochemical tongue of the invention display distinct electrical resistivities in the range from 1 to 5,000 ohms, e.g., 1000-2000 ohms.

FIG. 3 provides a schematic illustration of the electrochemical sensor according to the invention and a detection device into which the sensor is incorporated, i.e., either a portable device or a fixed device placed in a lab etc.

The dimensions of the sensor (1) are not critical; for example, in some embodiments it could easily fit into microfabrication-based configurations, which may be desirable because the volumes of biofluids available for measurements are often quite small. In the illustrative geometry that is shown in FIG. 3 the sensor possesses a cylindrical symmetry, with the electrodes being mounted in a tubular body (2) that is made of a suitable materials such as silicon, polyvinyl alcohol, and polydimethylsiloxane. For example, the tubular body is 2 to 5 cm long and its diameter is in the range from 2 to 3 cm. The electrodes extend along the tubular body; reference electrode (3) is concentrically and coaxially positioned along the symmetry axis of the tubular body; annular counter electrode (4) encircles the reference electrode (3). Multiple working electrodes (5) are positioned in radial direction from reference (3) and counter (4) electrodes and are evenly distributed along the perimeter of the cylindrical body.

When put to use, the electrochemical sensor (1) is immersed in the solution to be analyzed such that the base of the cylinder that is shown in the figure is exposed to the solution allowing the electrodes that (optionally) protrude from the base to be dipped into the liquid sample, creating the electrochemical cell for the measurements. It should be pointed out that the incorporation of a reference electrode in the electrochemical sensor is not mandatory, either because a two-electrode measurement technique may sometimes be employed, or because a reference electrode can be immersed in the solution externally to the electrochemical sensor of the invention.

The opposite base of the cylindrical electrochemical sensor (1) (not shown) provides the electrical wiring (6) to the control unit (7) which shall be described in some detail below.

The device may further comprise a liquid sampling unit (not shown) which includes a sample holder for holding a volume of the liquid to be analyzed and conventional means for feeding the liquid to the sample holder and discharging the liquid sample (e.g., a pump for driving the liquid through a suitable tube) and means for filtering the liquid to remove unwanted components prior to its introduction into the sample holder (e.g., a filter such as mesh sieve, fabric filter etc. with pore sizes intended to serve the filtration purpose).

It is noted that the device may be powered (8) by a battery or alternatively, can be connected to a main power supply. The control unit (6) is designed to serves several purposes.

For example, the flow of the liquid to the sample holder via a pump is controlled; the pump may be responsive to signals indicating that a sufficient amount of the liquid has been added to the sample holder (i.e., a fluid level switch), to halt the operation of the pump and prevent to excessive filling of the sample holder.

Another major function of the control unit (6) is of course to control the potential of the working electrodes or the current flowing through the cell, respectively, according to the chosen electrochemical technique. To this end, the device comprises either a potentiostat and/or galvanostat (7). For example, voltammetry-based methods (that is, with the aid of a potentiostat) have been shown to be efficient techniques in determining the concentrations of neurotransmitters in a biofluid.

The device may further include a data storage unit or a data transmitting unit (10), i.e., wired transmitter or a wireless network transmitting unit with conventional communication ports to deliver the data to an externally located data storage unit. A data storage unit may be the memory of the data processing unit or any computer readable media. In FIG. 3, personal instruments (12) are shown and also a cloud-based data storage system (13).

The device further comprises a processor (11) for analyzing a data set of electrochemical signals by one or more chemometric techniques, e.g., multivariate methods such as a supervised machine learning model (artificial neural network (ANN)), or a regression model, e.g. partial least square regression (PLSR).

Briefly, PLSR is a linear regression method and PLSR algorithms are available (e.g., MATLAB). As to ANN, a neural network model is generated with the aid of a training set. To this end, a matrix consisting of a large number of samples with known concentrations of the analytes (e.g., mixtures of neurotransmitters dopamine and norepinephrine, and optionally the interferant uric acid) and with known outputs is collected. As explained in more detail below, the data set is split to create a training set, a cross-validation set and a test set. In the training process, the error between the outputs predicted by the neural network and the known outputs is calculated; this process continues, with the algorithm adjusting the parameters iteratively to minimize the error, i.e., to reduce the error below an acceptable level. Once created, the model is saved and can be used for future measurements of test samples.

It should be noted that raw test data collected by the electrochemical sensor (e.g., a biofluid sample taken from a patient) undergoes pre-processing with the aid of known techniques before it is fed to the algorithm. Then methods such as principal component analysis (PCA), Fast Fourier Transform (FFT), and selection of important electrochemical signal features, can be used to reduce the dimensions of the data fed to the model. The latter method has been shown to be especially useful; the features selected (e.g., from the voltammograms) include peak current, peak potential, maximum slopes of the I vs. E function (for the increasing and decreasing parts of the function).

That is, to make a measurement of a test sample—using voltammetry for example—the sample is placed in the sample holder in contact with the electrochemical sensor in the device of the invention, as described above, varied voltage is applied by the potentiostat between the reference electrode and working electrode, currents generated are measured and the measurements are stored, and the test data collected (readings from all working electrodes) is preprocessed, reduced and scaled, fed to the ANN algorithm and the concentration of analyte is quantified.

One useful aspect of the invention is that the raw test data collected from a biofluid (i.e., from patients) can be used to calibrate the ANN trained model (that was previously trained using non-biofluid samples, e.g., samples prepared in buffer solutions, as shown by the experimental results reported below).

The two approaches for model building—PLSR and ANN are now discussed in more detail; the major steps are outlined below and are further exemplified in the Examples below. In both cases, data reduction is based on signal features.

Model Building Process—Based Signal Samples (PLSR)

1. Organization of data in a cell structure—with the aid of MATLAB software reading csv files, all experimental data is arranged in one type of structure (e.g. cell type).

2. Signal smoothing—By using the signal processing toolbox, MATLAB software 2017a version, a built-in function (e.g. 'filter') was used to filter the signals by employing a moving average window in order to reduce signal fluctuations and noisy behavior which is not originated by the electrochemical properties of the tested solution. A varied filter order in the range of 5<M <8, (M—filter order), depending on the noise level in the recorded data, was used. In order to keep this parameter as unbiased for all the recorded signals in each experiment, it was kept fixed and equal to specific value for each experimental data.

3. Baseline subtraction—In an electrochemical analysis, the main interest is the faradaic current that is generated owing to the electron transfer from the analyte to the electrode surface in a specific electric potential (oxidation potential). In order to improve signal to noise ratio (SNR), the Asymmetric least squares spline regression (AsLSSR) was used. With the aid of MATLAB software 2017a version, a function is built to estimate the baseline signal by getting two constant values parameters, $\lambda$ the smoothing parameter ($10^2 < \lambda < 10^9$) and p the asymmetry parameter ($0.001 < p < 0.1$). These two parameters take part in the numerical optimization of the cost function of the algorithm.

4. Organization of signals in a matrix structure—the signals are arranged in a matrix form, with each raw corresponding to specific array response. Signals were put in the matrix one after the other, to produce a super raw vector structure for each solution, while the target was defined as the concentration matrix, each column describing specific analyte concentration used through the experiments. This has been achieved by building MATLAB script (version 2017).

5. Dividing the data set into distinct subsets—The data is separated into two or three distinct sets. The first set is a training set, that is used for the training and the design of the model. All optimization procedures for finding the optimal solution are performed on the training set. It should be noted that the training set could be subdivided to create a small cross-validation set, as explained below and further illustrated in the Examples below. The other set is the test set. This set is used to check the model's generalization capabilities, by using the trained model in order to evaluate ability of the mode to predict the concentrations in the "unseen" samples. The data is usually divided as follows: 70-85% of the samples are assigned to the training set (including ~10% that may be used for cross-validation) and 10-30% for testing. The samples are divided randomly, but the computer's random generation is fixed to assure that the same subdivision could be reproduced.

6. Signals centering—In order to focus on the variability of each specific potential, data is centered, checking the average features value for the all set, and subtract it from the all signal, resulted with features with mean value equal to 0. The average value of the training set is saved for future use for centering the test set.

7. Choosing a regression model for prediction analysis— the partial least square regression (PLSR) model, a linear technique, was used. It is especially suitable for cases where there is a high correlation between the different features and when there is a limited number of samples (e.g. solutions). The 'plsregress' MATLAB function toolbox was used for model building and testing.

8. Choose optimal model parameters (k-fold cross validation)—In order to choose wisely different digital (e.g. number of latent variable in a PLSR model) and physical parameters (e.g. electrode combination) the CV method (LOOCV and 10-fold CV) was used. With the aid of a code that is able to give all the possible configurations without repetition, the CV was implemented in the MATLAB software 2017a version, using the 'cvpartition' function from the statistical toolbox, for random divisions into k sets. By dividing the train set and using it also for validation we were able to take advantage of most of the information hidden in the data. Model parameters minimizing the cross-validation error were chosen.

9. Model training—The best number of latent variables and best electrode combinations were chosen for training the model on all the training set. A PLSR model using the 'plsregeress' function from MATLAB statistics tool box (2017 version) was built.

10. Test Data pre-processing—The test signals were centered according to the mean average value of the training set.

11. Model predictability—The trained model was used to test and evaluate the performance on unseen data set, i.e., the test set, which was preprocessed and was ready for use as the model input.

12. Evaluate model performance—The quality of the model is assessed with the root mean square error between the known concentrations and those that were estimated by the model.

$$RMSE_{test} = \sqrt{\frac{1}{N_{test}} \sum_{i=1}^{N_{test}} (C_{expected} - C_{calculated})^2}$$

(N is the number of samples; $C_{expected}$ is the real actual value and $C_{calculated}$ is the predicted value).

Model Building Process—Based Direct Electrochemical Features (ANN)

1. organization of data in a cell structure—with the aid of MATLAB software, csv files are read, in order to arrange all the experimental data in one type of structure (e.g. cell type).

2. Signal smoothing—by using the signal processing toolbox, MATLAB software 2017a version, a built-in function (e.g. 'filter') was used to filter the signals by employing a moving average window in order to reduce signal fluctuations and noisy behavior which is not originated by the electrochemical properties of the tested solution. A varied filter order in the range of 5<M<8, (M—filter order), depending on the noise level in the recorded data, was used. In order to keep this parameter as unbiased for all the recorded signals in each experiment, it was kept fixed and equal to specific value for each experimental data.

3. Feature extraction—specific electrochemical signal features were extracted, i.e., features which are indicative of the identity of the redox-active molecule and its concentration in the solution. The extracted features include: peak potential, peak current, maximum slope of the signal, and current value at specific potentials (potentials which are known as the standard oxidation-reduction potential of specific analyte—good evaluation when the peak is not visible). All features extracted automatically using MATLAB software 2017a version built-in functions and by customary-built specific functions for each feature.

4. Organize features in a matrix structure—The extracted features were arranged in a matrix form, with each raw corresponding to specific array response, whereas each column describes specific analyte concentration through the experiment. This has been done by building MATLAB script (version 2017).

5. Dividing the data set into distinct subsets—The data is separated into two or three distinct sets. The first set is a training set, that is used for the training and the design of the model. All optimization procedures for finding the optimal solution are performed on the training set. It should be noted that the training set could be subdivided to create a small cross-validation set, as explained below and further illustrated in the Examples below. The other set is the test set. This set is used to check the model's generalization capabilities, by using the trained model in order to evaluate ability of the mode to predict the concentrations in the "unseen" samples. The data is usually divided as follows: 70-85% of the samples are assigned to the training set (including ~10% that may be used for cross-validation) and 10-30% for testing. The samples are divided randomly, but the computer's random generation is fixed to assure that the same subdivision could be reproduced.

6. Feature normalization—Features were standardized using the z-score transformation (subtracting the mean value of each feature, and scaling it by dividing the value by the standard deviation). Scaling was preformed because the features were in different scales, such as peak currents [$\mu A$] and peak potentials [V]. The data transformation was achieved with the aid of MATLAB software 2017a version. The transformation was performed on the training set, when the moments value were saved for future scaling of the test data.

7. Feature selection—The strategy employed for data reduction to decrease computational complexity was ten-fold cross-validation forward selection based linear regression. The criterion for the selection was the root mean square error between the "real" concentration and those estimated for the validation set. This was achieved with the aid of the statistical toolbox of MATLAB software 2017a version. In each the experiments we used a different initial number of features depending on the technique that was chosen to extract data features.

8. Choosing regression model for prediction analysis—In order to perform multivariate analysis (not only one target value), artificial neural network (ANN) models were used—a nonlinear techniques—to explore the relation between the extracted features to the neurotransmitters concentration. The ANN MATLAB toolbox was used to explore different network architectures.

9. ANN model optimization (based k-fold cross-validation)—Simple ANN architectures, such as 1-hidden layer with limited number of neurons, was used in order to reduce the chance for overfitting—the lesser number of neurons in use the lower network complexity. The best architecture was chosen with the aid of a cross-validation test: the number of neurons in the hidden layer was varied to test the network performance on a validation set. The upper bound of the number of neuros was set such that it is smaller than the number of the model weights. Then the number of neurons with the best score (in terms of the root mean square error between the known concentration and those who were estimated on the validation set) was chosen. The test was repeated with different initial conditions (e.g. different weight initializations), because ANN models are significantly affected by their initial conditions; but in each individual test the parameters were fixed in order to make unbiased and robust decision 10. Model training—having determined the best architecture, it was now used for training the model across the entire training set. The number of the training iterations was limited (early stopping) according to a specific error value that was set to stop the training procedure after reaching at least 99% of the target variance. Hence a trained network which minimizes the performance on the training data is created, ready for future testing.

11. Test data pre-processing—Based on the selected features in the feature selection procedure, the test features were loaded and standardized according to the training moments. For each feature, the training mean value was subtracted and the result divided it by the training standard deviation (this procedure is based on the fact that the two sets sampled from the same data population), creating a scaled data set.

12. ANN predictability—The trained model was used to test and evaluate the performance on unseen data set, i.e., on the test set which was preprocessed and was ready for use as the model input. Calculationa were performed in MATLAB software 2017a version, using the ANN toolbox function and aid function coded for specific tasks.

13. Evaluation of model performance—The quality of the model is assessed with the root mean square error (between the known $$RMSE_{test} = \sqrt{\frac{1}{N_{test}} \sum_{i=1}^{N_{test}} (C_{expected} - C_{calculated})^2}$$

(as previously defined) and the Pearson correlation coefficient (PCC):

$$PCC = \frac{E[C_{expected} - \mu_{expected}]E[C_{estimated} - \mu_{estimated}]}{\sigma_{expected}^2 \sigma_{estimated}^2}$$

EXAMPLES

Preparation 1

Bare Gold Electrodes

Commercial gold electrodes (disc-shaped, with radius equals to 1.5 mm) were polished with 0.05 μm alumina powder to obtain a mirror-shiny surface. The electrodes were rinsed with DI water and gently dried with kim-wipes™. The electrochemical activity of the electrodes was validated with the aid of cyclic voltammetry using the redox couple ferricyanide/ferrocyanide in a three-electrode arrangement cell consisting of the gold electrode, Pt counter electrode and Ag/AgCl reference electrode. 10 ml of 5 mM Ferrocyanide/Ferricyanide/10 mM PBS solution was added to the cell and the potential range −0.1V to +0.65V was scanned at a rate of 50 mV/sec (number of cycles 5). The expected anodic/cathodic peak current to be measured is about 0.83 μA. In case that the expected value is not measured, the rejected electrode is cleaned again (with the aid of polish kit with 0.05 μm polishing powder and micro-cloth polishing pad, followed by sonication, rinsing with methanol and drying). The cyclic voltammetry measurement is then repeated to verify the suitability of the electrode. If needed, 0.3 μm polish powder is used.

The electrodes are ready for use in the array of the invention, either as bare working electrodes or as base of the film-coated electrodes as described below.

Preparation 2

Preparation of Chitosan-Coated Gold Electrodes

Preparation of Deposition Solution (1% by Weight Chitosan Solution in Water)

7.5 g Chitosan (85% deacetylated) are added to 500 mL purified water. The solution is stirred for 3 hours, to achieve partial dissolution. Then 2M hydrochloric acid solution is slowly added until pH of 5-6 is reached; the volume of the acid that was added is about 14 ml. The solution was kept under stirring overnight. It was then filtered, to remove undissolved material, first with metal mesh then with stain-less steel mesh (0.106 mm mesh size, wire width 0.063 mm). The solution is stored at the refrigerator until use.

Electrodeposition of Chitosan Onto Gold Electrode

The electrodeposition was driven under constant current (chronopotentiometry technique) with the aid of a poten-tiostat (from BioLogic Science Instruments, controlled by EC-Lab® software), using two-electrode arrangement.

The polished working electrode of preparation 1 and the counter electrode (Pt wire) were immersed in a beaker into which 10 ml of the 1% chitosan solution were previously added. The current was set to −42 μA, creating a constant electrical flux of 6

$$\frac{\mu A}{mm^2}.$$

The negative current breaks the bonds of the water mol-ecules that cause for a pH changing and for a polymerization of the chitosan on the electrode surface.

Three chitosan-coated electrodes were prepared, with current duration of 1 min, 3 min and 5 minutes, respectively, to produce three electrodes with varying film thickness deposited on the electrode surface.

The coated electrodes were rinsed with water and placed in 10 ml PBS for one minute. The chitosan film-coated electrodes can now be used in the array of the invention.

Preparation 3

Carbon Nanotubes Incorporated-Chitosan-Coated Electrodes

Preparation of Deposition Solution (1% by Weight Chitosan Solution in Water +0.5% CNT, or 1.25% CNT, or 1.5% CNT)

CNT powder (multi-walled carbon nanotubes; Sigma-Aldrich) was added to 10 g of the chitosan solution prepared as described above, to obtain the deaired loading levels (that is, 0.05 g, 0.125 and 0.15 g CNT powder were added, respectively). The mixture was stirred for two minutes, then sonicated for forty minutes and stirred again, Electrodeposition of CNT-Added Chitosan Onto Gold Elec-trode The polished working electrode of preparation 1 and the counter electrode (Pt wire) were immersed in a beaker into which 10 ml of the deposition solution were previously added. The cathodic current was set to 6 A/m² and applied for 3 minutes.

Upon completion of the electrodeposition procedure, the electrodes were rinsed in DI water to remove unbound material. The CNT-incorporated, chitosan film coated-elec-trodes can now be used in the array of the invention.

Preparation 4

Preparation of Reduced Graphene Oxide-Coated Electrode

Preparation of Deposition Solution (0.5 mg/ml GO in Water)

27 ml of sulfuric acid solution (95-98 wt %) and 3 ml of phosphoric acid solution are mixed and the solution is stirred for several minutes. Then 0.225 of graphite powder is added under stirring. Next 1.32 g potassium permanganate is added slowly to the solution. The solution is allowed to stand under stirring for 6 hours and the color turns into dark green. Hydrogen peroxide 30% solution (0.675 ml)is added to eliminate excess potassium permanganate and the mixture is stirred for ten minutes. Next 5wt % hydrochloric acid (10 ml) and deionized water are added. The solid was separated by centrifugation at 5000 rpm for seven minutes. Residuals were repeatedly washed with hydrochloric acid and deion-ized water for three times. The washed GO solution was dried at 90° C. for twenty four hours and the powder was collected. Then 200 mg of the dried powder was mixed in 400 ml of deionized water to form the 0.5 mg/ml GO solution.

Electrodeposition of r-GO Onto Gold Electrode

The electrodeposition was driven under varying voltage (cyclic voltammetry technique) with the aid of the VSP300 potentiostat (Bio-Logic company) using three-electrode arrangement. 50 μl of the GO solution were added to the microelectrode chamber. Two cycles were performed: the potential from −1.6 V to +1.6 V was scanned at a rate of 50 mV/s.

The coated electrode was rinsed with deionized water and the coating was verified by performing cyclic voltammetry technique with a 5 mM ferrocyanide and 5 mM ferricyanide in 10 mM phosphate buffer solution. The r-GO film-coated electrode can now be used in the array of the invention.

Example 1

Fabrication of an Electrochemical Sensor Based on a Two-Working Electrode Array and Its Use in Measuring the Concentrations of Dopamine and Norepinephrine Electrochemical Measurements The working electrodes that were used to create the array were:

one bare Au electrodes of Preparation 1;

one chitosan-coated Au electrodes of Preparation 2 (the one obtained following three minutes electrodeposition time).

The electrochemical technique employed for the measurements was differential pulse voltammetry (DPV; pulse width: 5.0 ms, pulse height: 50 mV, step time: 10 ms, step height: 2 mV), using Bio-Logic VSP-300 potentiostat that supplied a staircase voltage signal and measure the electrical current in the solution. The three-electrode arrangement consists of Ag/AgCl electrode [saturated KCl] as a reference electrode, Pt wire as a counter electrode and as the working electrode, the bare and chitosan-coated electrodes mentioned above.

Validation of the Electrochemical Sensor

Bare Au Electrode

Figure 4A:
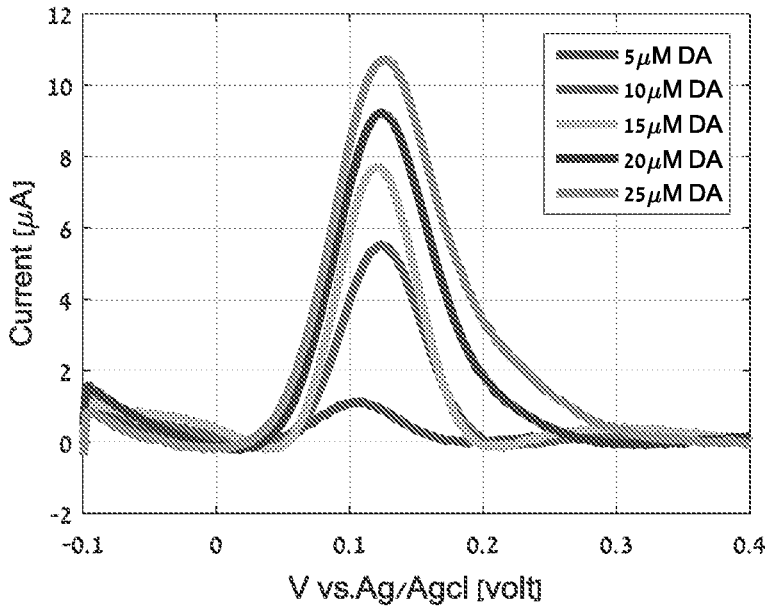
FIGS. 4A and 4B are current versus voltage plots measured using a bare Au electrode.
Figure 4B:
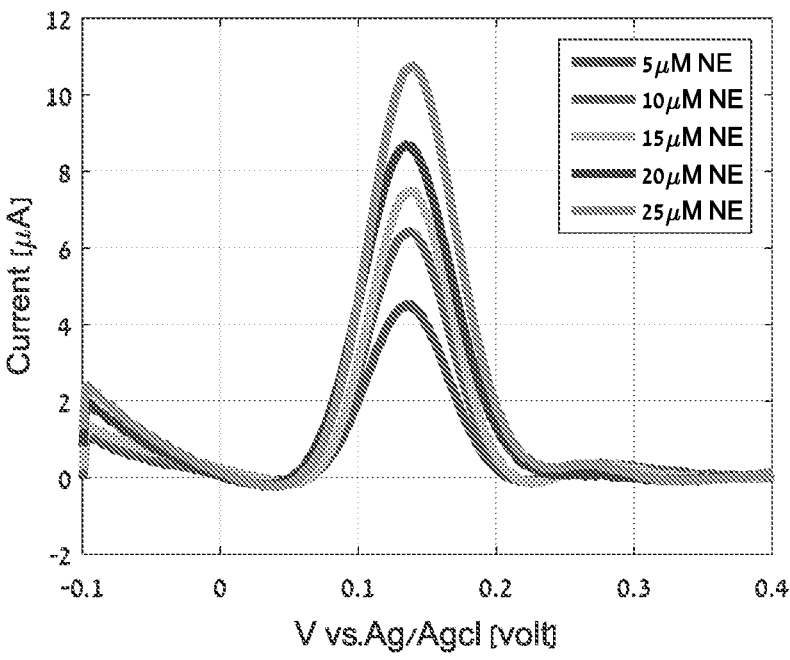
Figure 5A:
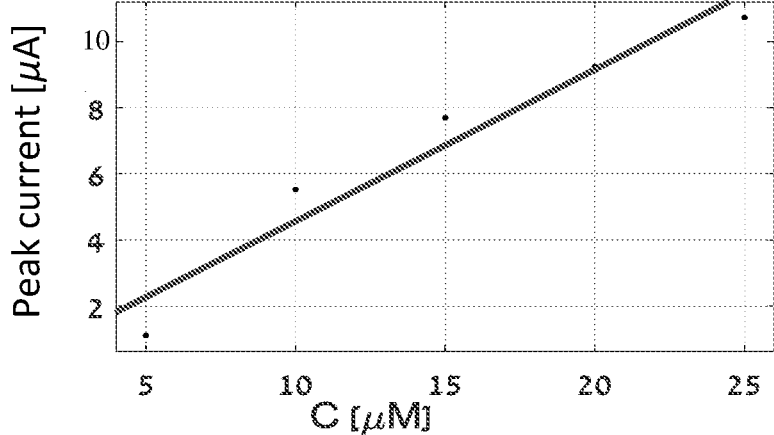
FIGS. 5A and 5B plots measured peak currents against the concentration of DA and NE in a solution using the bare Au electrode.
Figure 5B:
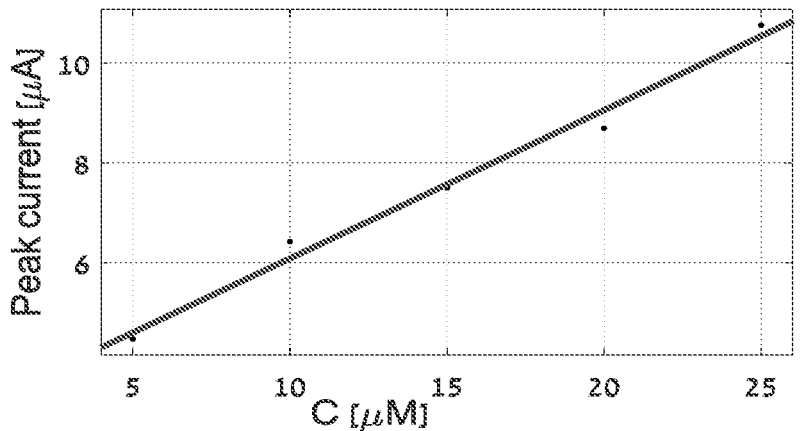

To validate the electrochemical system, the current measured by DPV using the bare Au electrode, for a set of DA solutions with varying concentrations (5 μM, 10 μM, 15 μM, 20 μM and 25 μM) and separately for a set of NA solutions with varying concentrations (5 μM, 10 μM, 15 μM, 20 μM and 25 μM) was recorded. Current versus voltage plots are shown in FIGS. 4A and 4B, for DA and NE, respectively. In FIGS. 5A and 5B, the measured peak currents ($I_{peak}$) were plotted against the concentration of DA and NE in the solution, showing, as expected, a linear relationship of $I_{peak}$ on the concentration for both molecules.

Furthermore, for NE, the theoretical slope of the $I_{peak}$ versus concentration linear function, based on known literature parameters, was calculated to be $0.292 \pm 0.06$ cm²/sec, in good agreement with the experimental slope that was found to be 0.239 cm²/sec, indicating that the system is able to measure DA and NE in different concentrations.

Chitosan Film-Coated Electrode

Figure 6A:
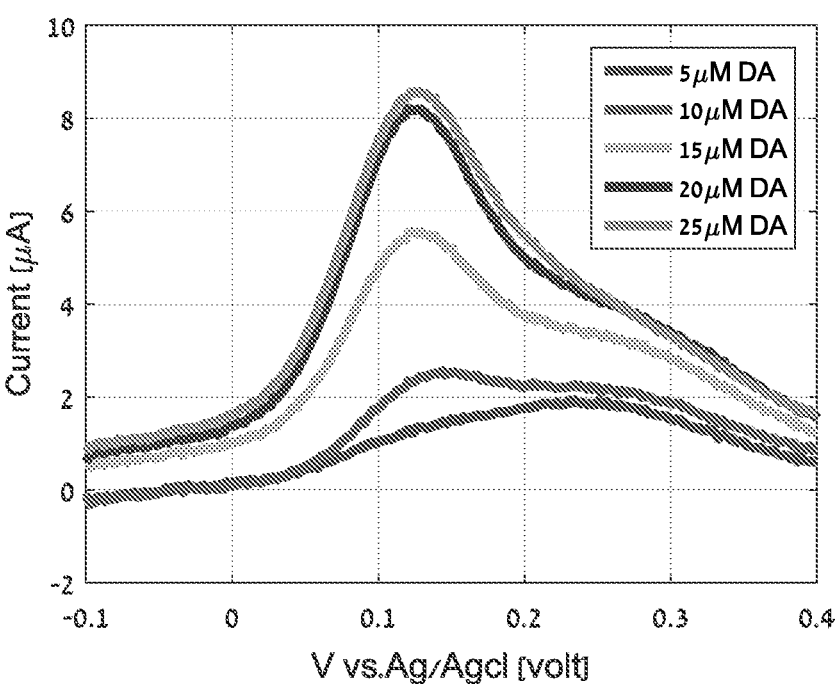
FIGS. 6A and 6B are current versus voltage plots measured using a chitosan film-coated electrode.
Figure 6B:
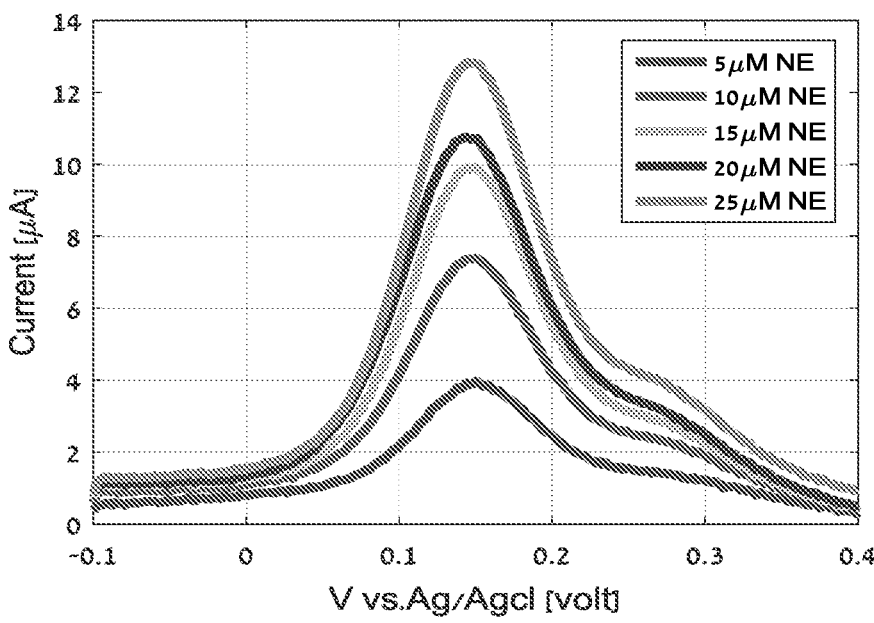

When the two separate sets of DA and NE solutions were tested by the DPV technique with the aid of the chitosan film-coated electrode, a different analyte response in comparison to the one generated by bare Au electrode was recorded, owing to the change of the sensing surface area properties. The corresponding current versus voltage plots are shown in FIGS. 6A and 6B, for DA and NE, respectively. It can be seen from FIG. 6A and 6B that the electrochemical signals measured with the chitosan-coated electrode are different from those measured using the bare electrode (FIGS. 4A and 4B). This variability forms the basis for the differentiation performance achieved by the array of the invention. It is also seen that DA was influenced strongly by the added chitosan, as indicated by the shift in position and shape of the current measured. On the other hand, NE signal does not seem to change in terms of shape and amplitude.

Creation of the Data Set

A matrix of solutions was prepared, each solution containing a mixture of DA and NE. A mixture is labelled $[C_{DA}]+[C_{NE}]$ to reflect the concentration of each component in a solution. The complete solution matrix consists of all possible binary combinations of the following concentrations:

DA: [$C_{DA}$=5, 10, 15, 20 and 25 μM]

NE: [$C_{NE}$=5, 10, 15, 20 and 25 μM]

Figure 7A:
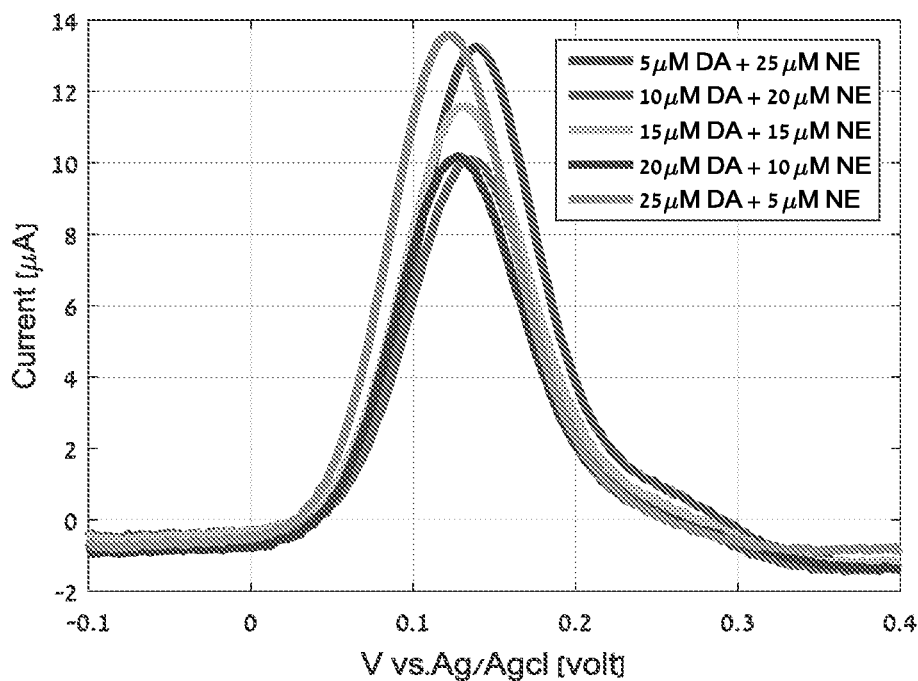
FIGS. 7A and 7B show current versus electrode voltage plots recorded for different solutions measured by the Au and chitosan-coated Au electrodes, respectively.
Figure 7B:
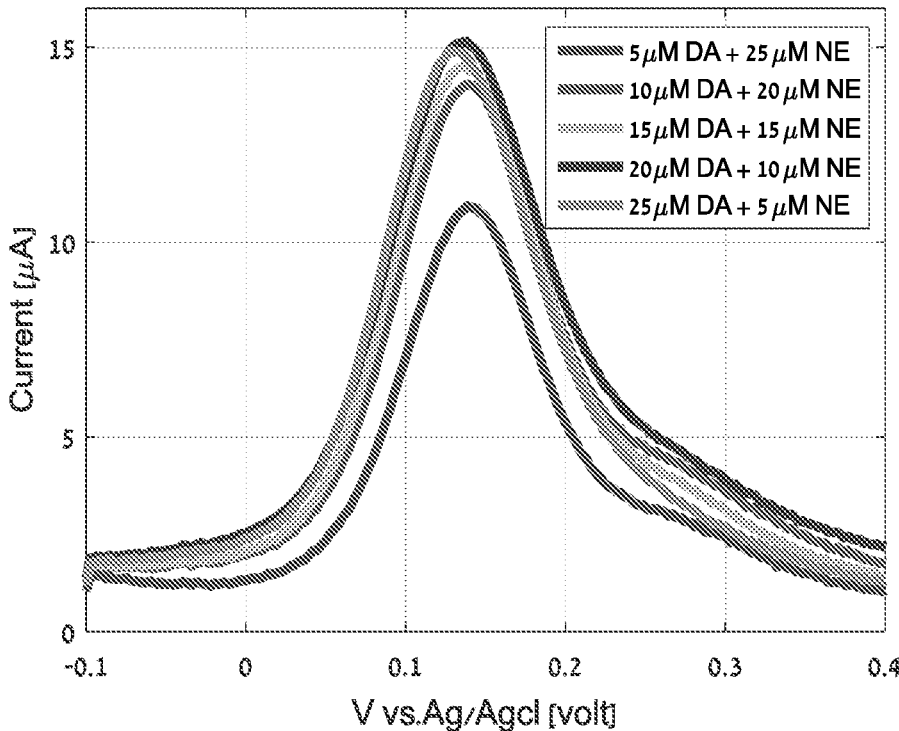

Each solution in the matrix was subjected to voltammetry measurement (DPV as described above), measuring the electrochemical signals of DA and NE from the two electrodes. Hence a set of electrochemical signals consisting of a total of 75 signals was created (triplicate repetition). FIGS. 7A and 7B show the current versus electrode voltage plots recorded for the following solutions by the Au and chitosan-coated Au electrodes, respectively:

$[C_{DA}$=5 μM]+[$C_{NE}$=25 μM];

$[C_{DA}$=10 μM]+[$C_{NE}$=20 μM];

$[C_{DA}$=15 μM]+[$C_{NE}$=15 μM]];

$[C_{DA}$=20 μM]+[$C_{NE}$=10 μM]; and $[C_{DA}$=25 μM]+[$C_{NE}$=5 μM]

Data Pre-Processing

The signals were organized in a structure allowing an efficient analysis. The matrix structure that was chosen in shown in FIG. 8. By using this type of matrix, it is possible to focus on the variance between the different rows in the matrix.

PLSR for the Estimation of DA and NE Concentration in a Mixture

Choosing Number of PLS Components—

Figures 8, 9:
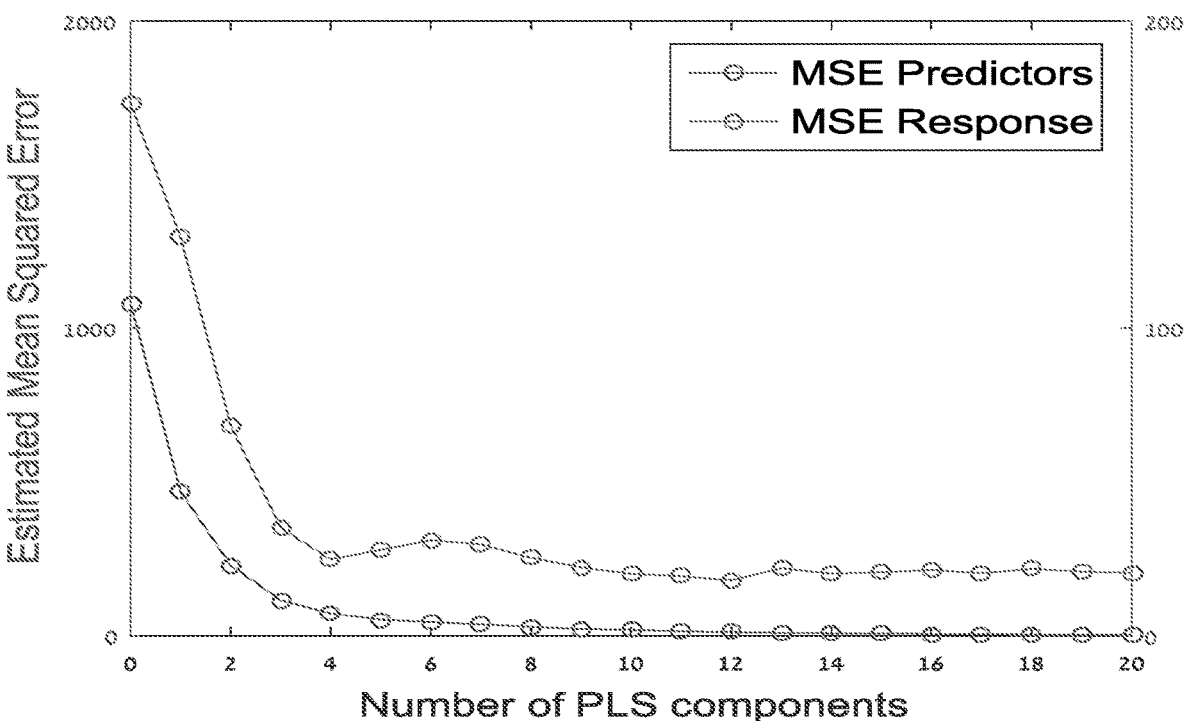
FIG. 8 shows the matrix structure that was chosen.
FIG. 9 plots man squared error versus the number of partial least square components.

The number of PLS components was determined with the aid of a cross-validation method, dividing the data set into three subset: a training set, a cross-validation set and a test set. The training set was used for the model building while the cross-validation set was used for testing model prediction ability, that is, testing different performance ability on this set in order to choose the best model parameters. Performance ability was determined by calculating the mean square error (MSE) between the estimated concentrations of the cross-validation set and the known concentrations. So, the number of PLS components was varied, and each time a new PLSR model was created and the MSE between the known concentrations and those that were estimated by the model were determined. The cross-validation performance indicates that ten PLS components suits the data well, as shown in FIG. 9, where the MSE is plotted against the number of PLS components. MSE decreases with increasing number of PLS components, but it is seen that moving beyond ten components gains no advantage. Thus, having decided on the number of the PLS components, the model was created based on the chosen number (10).

Model Estimation—

The next step is to predict the concentration of the test set with the aid of the so-formed model. That is, by applying the model on the test data set and calculate the root mean square error prediction between the known concentrations in the solutions of test set and those predicted by the model:

$$RMSE_{test} = \sqrt{\frac{1}{N_{test}} \sum_{i=1}^{N_{test}} (C_{expected} - C_{calculated})^2}$$

Figure 10A:
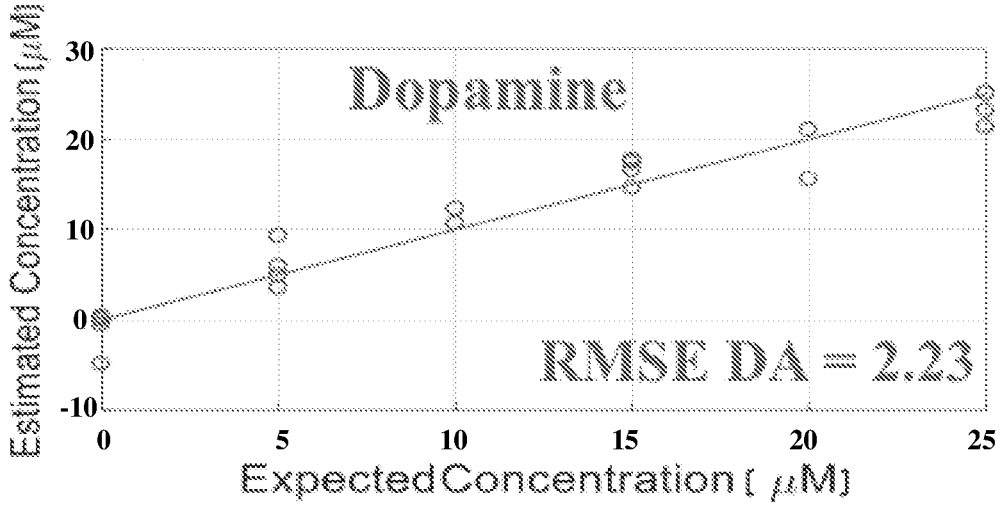
FIG. 10A and 10B plot estimated concentration versus expected concentration for DA and NE, respectively.
Figure 10B:
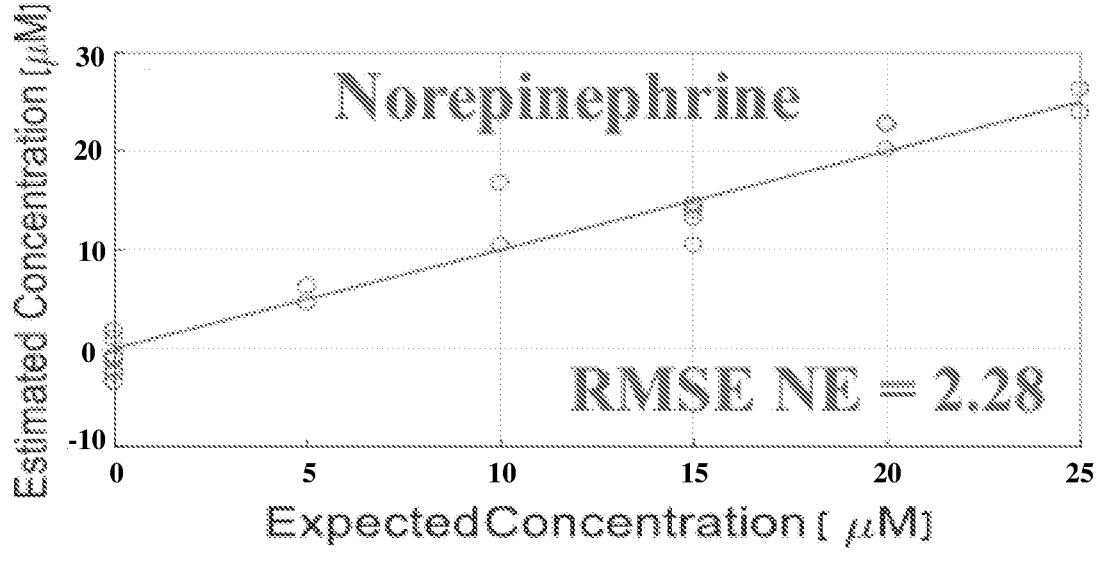

The data is show in in FIGS. 10A and 10B, for DA and NE, respectively, where the abscissa is the expected concentration (true concentration) and the ordinate is the estimated concentration calculated by the model. The ideal linear relationship is of course the Y=X straight line (calculated concentration equals to expected concentration). The results shown in FIGS. 10A and 10B indicate the efficiency of the PLSR-based approach.

ANN for the Estimation of DA and NE Concentration in a Mixture

ANN performance was tested on three different data sets: PCA features, FFT features and electrochemical features.

ANN Architecture—

For the model architecture, hidden layer with seven neurons was used, but the input layer was varied (three different input layers were tested) and the architecture was validated to determine the best input features.

In the first test (FFT), we used the ten dominant FFT coefficients, this by taking the FFT coefficient which has the biggest amplitude (indicative of the most dominant frequencies of the signal). Choosing number of components was based on signals visualizing in the frequency domain.

In the second test (PCA), the required percentage of explained variance by the model was set to 95%, and we checked how many is PC required to meet this threshold. It has been found that nine components are required; the PC scores where used as input of the first layer of the net.

In the third test, direct electrochemical features which were extracted automatically by specific functions that were built in MATLAB software 2016a version, were used. These features include: peak current, whose magnitude depends linearly on the concentration of the redox active molecule; peak potential, which is characteristic of the identity of the tested analyte (each analyte has is specific oxidation-reduction potential); charge in peak interval (related to the transfer rate of the electron to the electrode surface), derivative of current values which indicates current variation between different voltage values; and the potentials where the current peak start to rise and where is ends its descending.

ANN Model Estimation—

Model performance was evaluated by calculating RMSE and the Pearson coefficient between the known concentrations and those predicted by the model. The results are tabulated below:

TABLE 1

| Model type | RMSEP DA | RMSEP NE | Pearson coefficient DA | Pearson coefficient NE |
|---|---|---|---|---|
| FFT + ANN | 1.70 | 2.58 | 0.98 | 0.93 |
| PCA + ANN | 3.07 | 2.32 | 0.93 | 0.97 |
| Direct signal features + ANN | 2.26 | 2.27 | 0.97 | 0.97 |

The tabulated results indicate the direct signal features-based ANN has better performance. This model seems to offer a promising technique for electronic tongue application, using a prior knowledge according to the physical system.

Example 2

Fabrication of an Electrochemical Sensor Based on a Six-Working Electrode Array and Its Use in Measuring the Concentration of Dopamine in the Presence of Norepinephrine and Uric Acid Electrochemical Measurements The working electrodes that were used to create the array were:

two bare Au electrodes of Preparation 1;

two chitosan-coated Au electrodes of Preparation 2 (3 min. electrodepostion time); and two 1% CNT-incorporated chitosan-coated Au electrodes of Preparation 3.

Reference electrode (Ag/AgCl) and counter electrode (Pt wire) were washed with DI water. All electrodes were fitted into a circular stand; identical electrodes were "diametrically opposed" i.e., were placed on opposite ends of the diameter of the circular stand. The experimental set-up is shown in FIG. 11. The counter electrode is in the center; positions 1 and 5 are occupied by bare electrodes, indicated hereinafter $Bare_1$ and $Bare_2$, respectively; positions 2 and 4 are occupied by the chitosan-coated electrodes, indicated hereinafter $Chit_1$ and $Chit_2$, respectively; and positions 3 and 6 are occupied by the CNT-added chitosan coated electrodes, indicated $Chit\text{-}CNT_1$ and $Chit\text{-}CNT_2$, respectively. The reference electrode is also shown (R). The electrodes were electrically connected to a potentiostat that was connected to a computer. The electrochemical technique that was used for the measurements was DPV as described in more detail below.

The study reported herein is divided into two parts. In the first part, a model is developed to enable the detection of DA in the presence of NE and UA. In the second part, the model is used to measure DA in undiluted urine samples.

PART A: Detection of DA in the Presence of Masking UA+NE

Creation of a Set of Training Data for ANN Training

A set consisting of 216 mixtures of dopamine (DA), norepinephrine (NE) and uric acid in urinary physiological levels were prepared (3×6×6=108, by duplicate repetition). To this end, the following stock solutions were prepared (DA molecular weight=153 g/mole; NE molecular weight=169.14 g/mol; UA molecular weight=168.11 g/mole):

750 µM stock solution of DA was prepared by dissolving 3 mg of DA in 0.21 ml of 10 mM PBS to obtain 75 mM stock solution. An 100 µL aliquot was taken from the 75 mM stock solution and added to 9.9 ml PBS to obtain 10 ml of 750 µM stock solution of DA.

150 µM stock solution of NE was prepared by dissolving 3 mg of NE in 1.18 ml of 10 mM PBS to obtain 15 mM stock solution. An 100 µL aliquot was taken from the 15 mM stock solution and added to 9.9 ml PBS to obtain 10 ml of 150 µM stock solution of DA.

Several stock solutions of UA were prepared; First, 10 mM stock solution was prepared by dissolving 504.33 mg of UA in 300 ml of 10 mM PBS.

An 45 mL aliquot was taken from the 10 mM UA stock and added to 555 ml PBS to get 600 ml of 750 µM UA stock solution. An 90 mL aliquot was taken from the 10 mM UA stock and added to 510 ml PBS to get 600 ml of 1500 µM UA stock solution. An 120 mL aliquot was taken from the 10 mM UA stock and added to 480 ml PBS to get 600 ml of 2000 µM UA stock solution.

Next, a matrix of mixtures was prepared using the stock solutions. A mixture is labelled $[C_{UA}][C_{DA}][C_{NE}]$ to reflect the concentration of each component in a solution. The complete solution matrix consists of all possible ternary combinations of the following:

UA: $[C_{UA}=750, 1500$ or $2000$ µM]

DA: $[C_{DA}=0, 0.25, 0.5, 0.75, 1.0$ or $1.25$ µM]

NE: $[C_{NE}=0, 0.05, 0.1, 0.15, 0.2, 0.25$ µM]

The voltammograms were obtained by connecting a IviumStat potentiostat to multiplexer MultiWE32 that supplied an identical staircase voltage signal to all six channels simultaneously and measured the electrical current in the solution in each one of the electrodes; differential pulse voltammetry was used (DPV; pulse width: 1 msec, pulse height: 55 mV, scan rate: 10 my/sec, step height: 2 mV, Equilibration time—60 sec, current range—10 µA). FIG. 12 shows the electrochemical signals recorded for the 216-containing set of samples.

Model Building

The approach is based on extraction of direct electrochemical features.

Feature Extraction—

Figure 13:
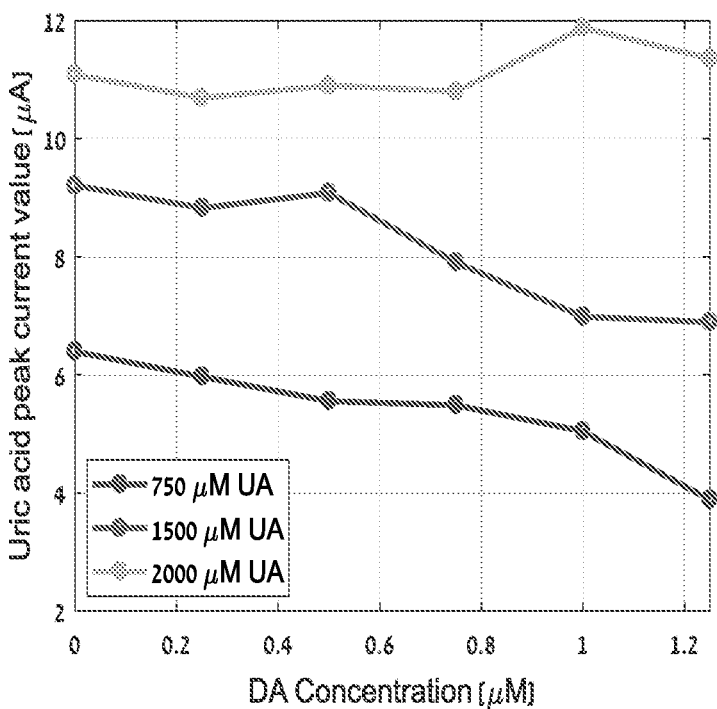
FIG. 13 shows how uric acid peak current is varied dependent on DA concentration

An interesting behavior was noted from the raw data: the peak current of UA oxidation varied in samples having the same concentration of UA, suggesting that it may be possible to decipher some relevant information related to the variation of DA concentration. This is better illustrated in FIG. 13, which shows how UA peak current is varied dependent on DA concentration. For 750 and 1500 µM UA concentration, a negative correlation is noted. When UA concentration was increased (e.g. 2000 µM), the effect becomes negligible.

Eventually a total of twenty four features were extracted, four for each electrode. The features were: peak current, peak potential, maximum slopes of the I vs. E function (for the increasing and decreasing parts of the function).

Feature Selection—

Figure 14:
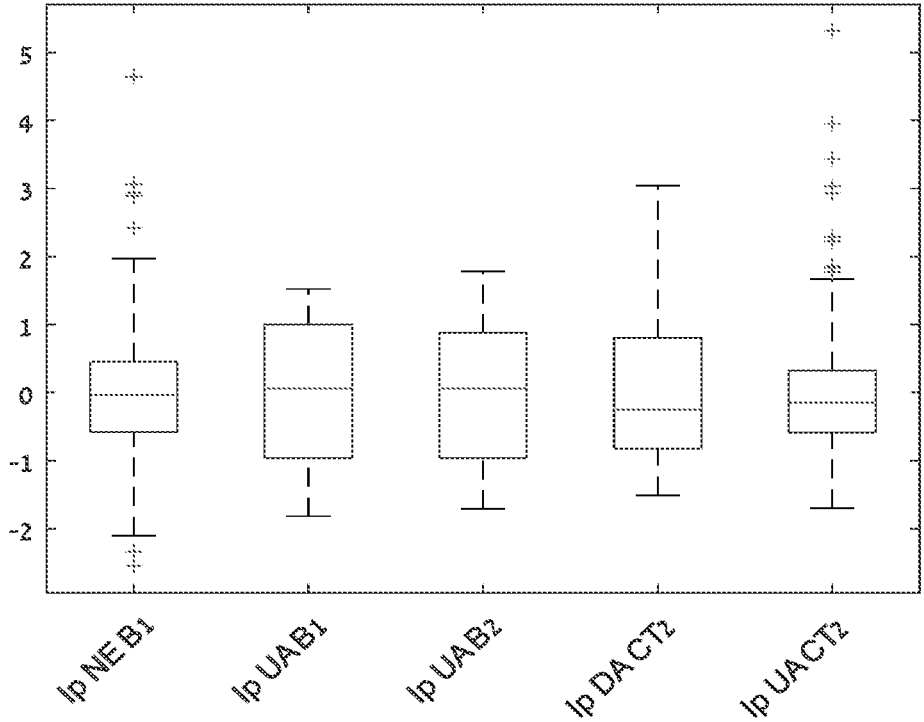
FIG. 14 shows the best features that were identified from a forward selection based 10-fold cross validation linear regression.

Next, a forward selection based 10-fold cross validation linear regression was performed; the five best features that were identified are shown in FIG. 14 (Ip is the peak current for the analyte measured by the electrode; $B_1$ and $B_2$ are $Bare_1$ and $Bare_2$ electrodes mentioned above; $CT_2$ is the $Chit$-$CNT_2$ electrode mentioned above). It is seen from FIG. 14 that all five selected features refer to current values at different electrodes, suggesting that the variation of UA peak value, and its specific value, decipher some new information related to variation of DA concentration. That is, useful information about the analyte of interest, DA, may be obtained by exploring the noise component (e.g. UA), rather than by looking for a way to reduce it. DA and NE peak currents in specific values were found also as variables which significantly contribute to the concentration prediction of DA. It is noted that the selected features were received from the bare and the chitosan-CNT electrodes, suggesting that the dominant differentiation mechanism depend strongly on the change of electron transfer rate of the molecules and not on the molecular weight and size (DA, NE and UA have similar MW—153, 169, 168

$$\frac{gr}{mol}$$

respectively).

ANN Model Architecture— ten-fold cross-validation test was performed, changing the number of the neurons in the (single) hidden layer. We used the minimization of the mean square error between the known concentrations and those that were estimated by the model upon variation of the number of neurons in the hidden layer in order to decide on the best architecture. The results are shown in FIG. 15, where the validation error is plotted against the number of neurons in the hidden layer. The optimal number is thirteen, minimizing the cross-validation error. Hence, the architecture chosen was a fully-connected 5-13-1 network.

ANN Model Performance

The next step is to apply the 5-13-1 model to a test set. The following test set was used:

$[C_{NE}=0.2][_{DA}=0.75][C_{UA}=1500]$ $[C_{NE}=0.15][C_{DA}=0.25][C_{UA}=750]$ $[C_{NE}0.11][C_{DA}=0.75][C_{UA}=1500]$ $[C_{NE}=0.05][C_{DA}=1.0][C_{UA}=2000]$ $[C_{NE}=0.25][C_{DA}=1.25][C_{UA}=750]$ $[C_{NE}=0.2][C_{UA}=0.75][C_{UA}=2000]$ $[C_{NE}=0.175][C_{DA}=1.125][C_{UA}=1800]$ $[C_{NE}=0.125][C_{UA}=0.6][C_{UA}=1000]$ $[C_{NE}=0.225][C_{DA}=0.8][C_{UA}=1250]$ $[C_{NE}=0.075][C_{DA}=1.20][C_{UA}=800]$

The test data was recorded and preprocessed, reduced by taking the best features as determined above and normalized based on the training average and STD values per each feature. The Levenberg-Marquardt method for model optimization was used. A stop criteria was set (model explains 99% of target variability).

FIG. 16A and 16B graphically illustrates the performance of the model, in the form of estimated (model-predicted) concentration versus expected (real) plot. The plots, provided for both the training and the test sets (FIGS. 16A and 16B, respectively), show fairly close RMSE and PCC values; data is also tabulated below in Table 2.

TABLE 2

|  | PCC | RMSE |
| --- | --- | --- |
| DA (train set) | 0.932 | 0.152 |
| DA (test set) | 0.945 | 0.138 |

The results indicate that the ANN model-based sensor array is able to estimate DA concentrations also in a fully-masking environment.

Part B: Prediction of DA Concentration in Urine Samples

The next challenge was to test the model—which was trained on non-urine data, namely, neurotransmitters added PBS (Phosphate buffered saline)—on DA and NE-spiked urine samples. The urine samples were taken from two healthy volunteers.

Figure 17:
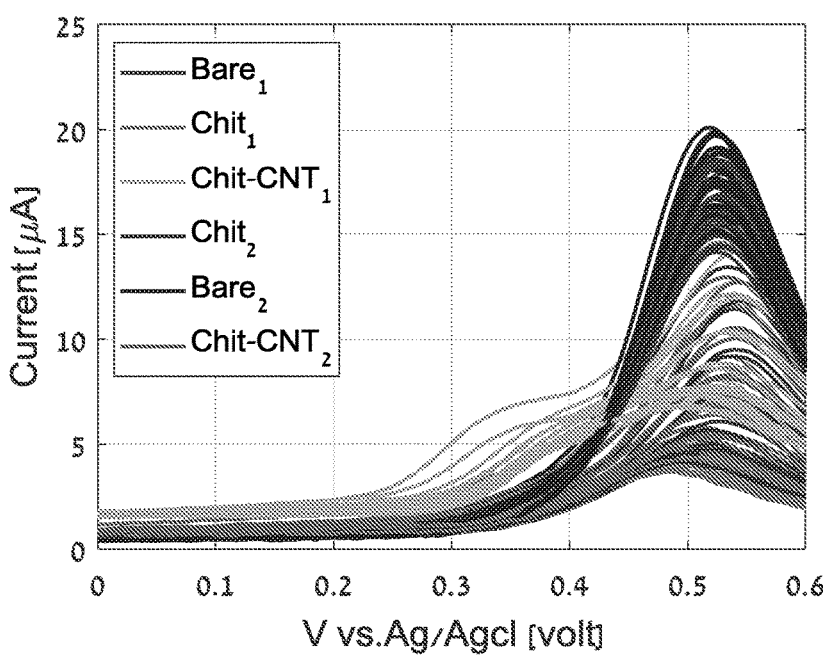
FIG. 17 shows raw data electrochemical signals recorded from collected urine samples, using a differential pulse voltammetry technique.

The DA and NE spiked-urine samples were prepared as follows. Stock solutions with varying DA concentrations were prepared. Separately, stock solutions with varying NE concentrations were prepared. 5 ml urine was placed in 15 ml tube. A volume 200 µL was expelled. 100 µL aliquot taken from DA stock solution, and 100 μL aliquot taken from NE stock solution was added to the sample, to create a set of sample with DA and NE concentrations varying in the range of 0-20 μM. Five samples were taken from each patient; one patient data was used for the calibration of the model, and the second one was used to test model performance. Raw data electrochemical signals recorded from the collected urine samples, using differential pulse voltammetry technique, are shown in FIG. 17 (current versus potential plots).

Novel Approach to Model Building

The data that was recorded from PBS solutions in Part A, and the data that was recorded from urine samples constitute different data populations, and hence are not expected to exhibit exactly the same behavior. The major differences between the PBS and urine environments include solution pH and number of electroactive species present in urine tending to donate an electron through the application of oxidizing current. Another main factor is the high variability of different patients: different patients have different eating and consumption habits, which can lead to significant variability in urinary electrochemical active molecules, creating different patterns.

Figure 18:
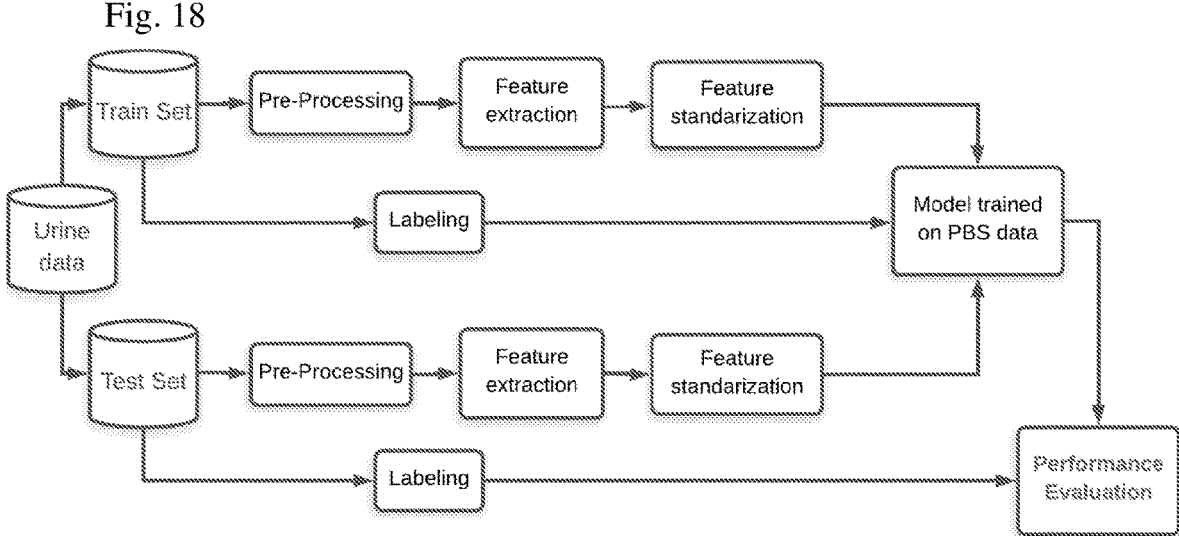
FIG. 18 illustrates a methodology for building a predictive model for urine samples.

However, despite the difficulty mentioned above, it is postulated that by application of systematic changes in the neurotransmitter concentrations, urine training samples and PBS training samples should still respond in a correlative manner. This assumption forms the basis for the proposed approach towards overcoming the problem. The approach is shown in FIG. 18, illustrating a methodology for building a predictive model for urine samples.

The urine data set is split into a training subset and a test subset. Each subset is individually preprocessed using a six order averaging window for signal smoothing; features are extracted according to the model building described in part A, and normalized. Next, the trained model based on the PBS data that was created in PART A is applied for a new training session using a stop criteria based on the error on the training data (as was mentioned earlier). Having trained the model, it is applied to the test set for assessment of model performance. The major steps are described below.

Feature Extraction and Selection—

The same features discussed in Part A were extracted and selected for the final prediction. The features were arranged in a matrix set and standardized based on the patient data.

Model Performance

Figures 19A, 19B:
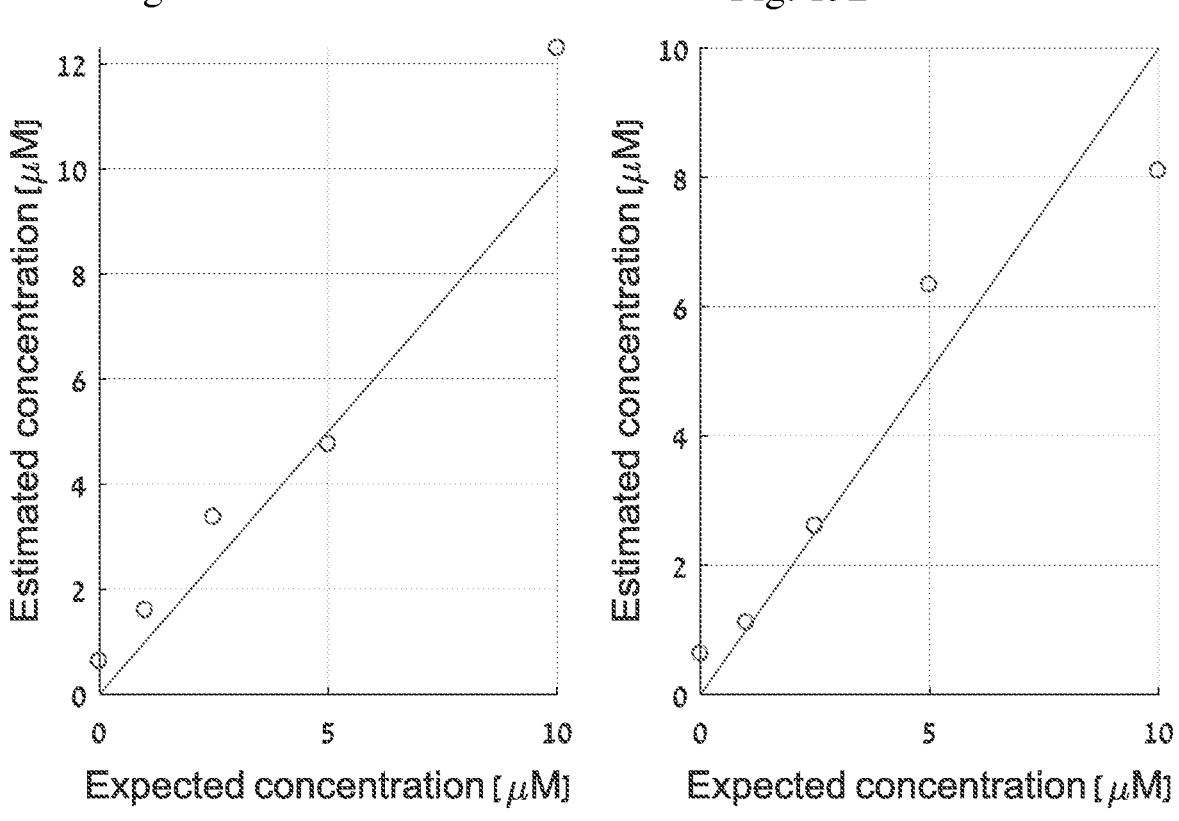
FIGS. 19A and 19B plot estimated concentration versus expected concentration for training and test sets, respectively.

Model performance was assessed based on RMSE and PCC, as previously explained in Part A. The results are presented graphically for the training and test sets (FIGS. 19A and 19B, respectively), where the estimated concentration is plotted against the expected concentration. Data is also tabulated below in Table 3.

TABLE 3

| | PCC | RMSE |
|---|---|---|
| DA (urine train set) | 0.967 | 1.07 |
| DA (urine test set) | 0.987 | 1.15 |

The fairly close values that were obtained indicate the efficacy of the proposed approach. The proposed approach can be used as flexible calibration & testing method for point of care (POC) applications—performing an initial calibration for patient biomarkers (e.g. training) and real-time monitoring biomarkers levels (e.g. testing).

The invention claimed is:

1. An electrochemical sensor comprising one counter electrode, optionally a reference electrode, and an array of multiple working electrodes, wherein the array of working electrodes comprises:

a first subarray consisting of one or more bare electrodes;

a second subarray consisting of one or more film-coated electrodes;

a third subarray consisting of one or more conductive additive-incorporated film-coated electrodes;

wherein a film-forming material has a repeat unit that comprises a six-membered non-aromatic ring such that the film coated electrodes are partially selective and can cross-react with multiple redox molecules.

2. An electrochemical sensor according to claim 1, wherein the six-membered, non-aromatic ring bears amine group, carboxylic acid group, hydroxyl group or sulfonic acid group covalently bonded to a carbon atom of said ring.

3. An electrochemical sensor according to claim 1, wherein the film-forming material is polysaccharide.

4. An electrochemical sensor according to claim 3, wherein the polysaccharide is chitosan.

5. An electrochemical sensor according to claim 1, wherein the conductive additive that is incorporated into the one or more conductive additive-incorporated film-coated electrodes is carbon nanotubes.

6. An electrochemical sensor according to claim 1, wherein at least one of the working electrodes is a carbon nanotubes-incorporated chitosan-coated electrode.

7. An electrochemical sensor according to claim 1, wherein the working electrodes comprise:

one or more bare gold electrodes; and one or more chitosan-coated gold electrodes.

8. An electrochemical sensor according to claim 1, wherein the working electrodes comprise:

one or more bare gold electrodes;

one or more chitosan-coated gold electrodes; and one or more carbon nanotubes-incorporated chitosan-coated gold electrodes.

9. An electrochemical sensor according to claim 1, wherein the working electrodes comprise:

one or more bare electrodes;

one or more chitosan-coated electrodes;

one or more carbon nanotubes-incorporated chitosan-coated electrodes; and one or more reduced graphene oxide-coated electrodes; and wherein the film made of chitosan and the film made of reduced graphene oxide are electrodeposited films.

10. A method of electrochemical detection of one or more analytes in a liquid sample, the method comprising the steps of:

bringing a liquid sample into contact with an electrochemical sensor as defined in claim 1;

applying variable voltage, fixed voltage, current or impedance across the working electrodes;

measuring the current flowing or the impedance between each of the working electrodes and a counter electrode, or the potential between each of the working electrodes and a reference electrode, to obtain a raw data set consisting of plurality of electrochemical signals;

preprocessing the raw data set; and applying chemometric method(s) to the preprocessed data, to qualitatively or quantitively characterize the analyte of interest.

11. A method according to claim 10, wherein the liquid sample is a biofluid sample and the analyte is an organic redox compound, wherein an interferant is optionally present in said biofluid sample.

12. A method according to claim 11, wherein the analyte is a neurotransmitter.

13. A method according to claim 12, wherein the analyte of interest is dopamine and/or norepinephrine and the interferant is uric acid.

14. A method according to claim 10, comprising applying variable voltage and measuring current as the electrochemical signal.

15. A method according to claim 14, wherein the raw data is reduced in dimensions and normalized, the reduction being achieved using extracted electrochemical features recorded by voltammetry.

16. A method according to claim 15, comprising applying one or more chemometric method(s) selected from partial least square regression or a trained artificial neural network model (ANN).

17. A method according to claim 16, comprising applying trained artificial neural network model to the preprocessed raw data.

18. A method according to claim 17, wherein the raw data that is obtained from a biofluid is used to calibrate the model that was previously trained using non-biofluid samples.

19. A device for electrochemical detection, comprising:
one counter electrode, optionally a reference electrode, and an array of multiple working electrodes, wherein at least one of the working electrodes is a first film-coated electrode, with a film-forming material that has a repeat unit that comprises a six-membered non-aromatic ring, wherein the array of working electrodes further comprises at least one bare electrode and/or at least one second film-coated electrode that is different from the first film-coated electrode, wherein each film coated electrode is partially selective and can cross-react with multiple redox molecules;
a potentiostat or galvanostat to which the electrodes are electrically connected to allow control of the potential or current of the working electrodes, respectively, to create a data set of electrochemical signals when the electrodes are immersed in a sample; and
a processor configured to analyze the data set of electrochemical signals by one or more chemometric techniques.

20. A device according to claim 19, comprising the potentiostat, the potentiostat being configured to record current signals measured by voltammetry.

21. A device according to claim 20, wherein the one or more chemometric techniques include a regression method, a supervised or unsupervised machine learning algorithm, or both.

22. A device according to claim 21, wherein the regression method is partial least square regression (PLSR).

23. A device according to claim 21, wherein the supervised machine learning algorithm is a trained artificial neural network (ANN).

24. A device according to claim 20, wherein the processor is configured to reduce the dimensions of the data set by extracting electrochemical features recorded by voltammetry of a biofluid sample.

25. A device for electrochemical detection according to claim 19, wherein the array of working electrodes comprises the one or more bare electrodes.

26. A device for electrochemical detection according to claim 25, wherein the first film-coated electrode is coated with a chitosan film.

27. A device for electrochemical detection according to claim 25, wherein the array of working electrodes further comprises the at least one second film-coated electrode, each second film-coated electrode being a conductive additive-incorporated film-coated electrode.

28. A device for electrochemical detection according to claim 27, wherein each second film-coated electrode is coated with a carbon nanotubes-incorporated chitosan film.

29. A device for electrochemical detection according to claim 27, further comprising one or more reduced graphene oxide-coated electrodes.

\* \* \* \* \*